United States Patent [19]
Sheehan et al.

[11] Patent Number: 5,601,084
[45] Date of Patent: Feb. 11, 1997

[54] DETERMINING CARDIAC WALL THICKNESS AND MOTION BY IMAGING AND THREE-DIMENSIONAL MODELING

[75] Inventors: Florence H. Sheehan, Mercer Island; Edward L. Bolson; Huaichuan Jin, Seattle, all of Wash.

[73] Assignee: University of Washington, Seattle, Wash.

[21] Appl. No.: 451,757

[22] Filed: May 26, 1995

Related U.S. Application Data

[63] Continuation-in-part of Ser. No. 82,404, Jun. 23, 1993, Pat. No. 5,435,310.
[51] Int. Cl.$^6$ .................................................. A61B 8/00
[52] U.S. Cl. ........................... 128/661.04; 128/653.1; 128/660.07
[58] Field of Search ........................ 128/653.1, 661.04, 128/663.02, 660.07

[56] References Cited

U.S. PATENT DOCUMENTS

| | | | |
|---|---|---|---|
| 4,710,876 | 12/1987 | Cline et al. | 364/414 |
| 5,072,384 | 12/1991 | Doi et al. | 364/413.13 |
| 5,097,836 | 3/1992 | Yamada et al. | 128/661.04 |
| 5,151,856 | 9/1992 | Halmann et al. | 364/413.03 |
| 5,239,591 | 8/1993 | Ranganath | 382/6 |
| 5,273,038 | 12/1993 | Beavin | 128/653.1 |
| 5,273,040 | 12/1993 | Apicella et al. | 128/653.2 |
| 5,274,549 | 12/1993 | Almasi | 364/413.07 |
| 5,360,006 | 11/1994 | Geiser et al. | 128/653.1 |

OTHER PUBLICATIONS

J. Christophe Cauvin et al., "Automatic detection of the left ventricular myocardium long axis and center in thallium–201 single photon emission computed tomography," Original article, *European Journal of Nuclear Medicine*, Received Apr. 15, 1992 and in revised form Jun. 21, 1992, © Springer–Verlag 1992, pp. 1032–1037.

Potel et al., "Three–Dimensional Left Ventricular Wall Motion in Man Coordinate Systems for Representing Wall Movement Direction," Original Investigations, *Investigative Radiology*, vol. 19, No. 6, Nov.–Dec. 1984, pp. 499–509.

*Primary Examiner*—Marvin M. Lateef
*Assistant Examiner*—Derrick Fields
*Attorney, Agent, or Firm*—Ronald M. Anderson

[57] ABSTRACT

A method for imaging and three-dimensional modeling portions of the heart, particularly the left ventricular endocardial and epicardial surfaces, using imaging data. Preferably, a transesophageal ultrasound probe is inserted into an esophagus of a patient to provide multiple plane imaging data at end systole and end diastole during a cardiac cycle. The image planes are then traced along the boundaries of the epicardial and endocardial surfaces to produce sets of data points, which are further processed and expanded through interpolation. These data points are used for modeling the endocardial and epicardial surface at the end systole and end diastole extremes of the cardiac cycle. A center surface is constructed between an inner and outer surface of the modeled surfaces of the left ventricle and either an average template of tiled sections is mapped onto this center surface, or a mesh of triangular tiled sections representing the inner surface is projected on the center surface to define corresponding numbered tiled sections on the center surface. The tiled sections of the center surface are then projected onto the inner and outer surfaces, defining triangular prisms. By determining the volume of the triangular prisms and an average area for their ends, the range of movement, which is equal to the volume divided by the average area, is determined. Similarly, for changes in wall thickness between the endocardial and epicardial surfaces at end diastole and end systole, the thickening of the cardiac wall is determined.

26 Claims, 33 Drawing Sheets

356 ↘

358
MAP THE TILE TEMPLATE FROM THE AVERAGE CENTERSURFACE TO AN INDIVIDUAL PATIENT'S CENTERSURFACE USING A THIN-PLATE SPLINE INTERPOLATING FUNCTION.

360
CONSTRUCT A CHORD AT EACH CORNER OF EACH TILE, PERPENDICULAR TO THE AVERAGE PLANE OF ALL TILES CONVERGING ON THAT TILE. THE CHORD WILL EXTEND TO ITS INTERSECTIONS WITH THE MODELED END DIASTOLIC AND END SYSTOLIC SURFACES. THE POINTS OF INTERSECTION BETWEEN THE CHORDS AND EACH MODELED SURFACE EFFECTIVELY TRANSFER THE TILE TEMPLATE PATTERN FROM THE PATIENT'S CENTERSURACE TO THE PATIENT'S END DIASTOLIC AND END SYSTOLIC MODELED SURFACES.

362
CALCULATE THE REGIONAL WALL MOTION OF EACH TILE ON THE END DIASTOLIC MODELED SURFACE AS FOLLOWS:
1) CALCULATE THE VOLUME OF THE TRIANGULAR PRISM DEFINED BY ONE TILE ON THE END DIASTOLIC MODELED SURFACE, AND THE CHORDS THAT CONNECT THE CORNERS OF THESE TWO TILES.
2) CALCULATE THE AVERAGE AREA OF THE TILES ON THE END DIASTOLIC AND END SYSTOLIC MODELED SURFACES.
3) DIVIDE THE VOLUME OF THE PRISM BY THE AVERAGE TILE AREA. THE RESULT IS THE HEIGHT OF THE PRISM, WHICH IS THE EXTENT OF MOTION OF THE TILE FROM END DIASTOLE TO END SYSTOLE.

*FIG. 27.*

DETERMINING CARDIAC WALL THICKNESS AND MOTION BY IMAGING AND THREE-DIMENSIONAL MODELING

This invention was made with government support under HL 41464 awarded by the National Institutes of Health. The government has certain rights in the invention.

RELATED APPLICATIONS

This application is a continuation-in-part of prior U.S. patent application, Ser. No. 08/082,404, filed Jun. 23, 1993, now U.S. Pat. No. 5,435,310, issued on Jul. 25, 1995, the benefit of the filing date of which is hereby claimed under 35 U.S.C. § 120.

FIELD OF THE INVENTION

This invention generally relates to a method for imaging and modeling a heart in three dimensions, and more specifically, to a method for using a three-dimensional model of the heart to determine cardiac parameters.

BACKGROUND OF THE INVENTION

Monitoring certain parameters of left ventricular function can provide information useful for evaluating a patient's condition during surgical procedures. These parameters also provide information that can be used to detect coronary heart disease and other medical problems of the heart. One of the most commonly used parameters for diagnostic purposes is the left ventricular global ejection fraction, which expresses the proportion of chamber volume ejected with each heart beat. Other important parameters include the range of motion of the left ventricular wall and the thickening of the ventricular wall, both of which are indicators of coronary heart disease, and of other disease entities.

The effects of coronary heart disease are regional, being limited to the portion of the heart muscle receiving blood supply from an affected artery. When the internal diameter of an artery is reduced by atherosclerotic plaque, blood flow to the specific region of the heart supplied by that artery is restricted. As a result, some degree of dysfunction occurs in the affected heart muscle. During a heart attack, the affected muscle dies and is replaced by scar tissue, which is non-contractile. Thus, the progress of coronary artery disease is revealed by its effect on regional left ventricular function, and the severity of a heart attack is measured by the size of the dysfunctioning region and by the extent of the dysfunction. Similarly, any improvement of regional function in the affected portion of the left ventricle is an indication of the effectiveness of a prescribed treatment.

The appearance of dysfunction in a previously well-functioning ventricle is a serious warning that the blood supply is insufficient. Should a deterioration of function occur during surgery, it may be construed as an indication that the anesthesiologist should increase the fluid volume and/or engage in other corrective measures.

The detection of regional dysfunction has also been used during stress studies, wherein a patient's heart is imaged using ultrasound while at rest and after exercise, to determine whether the patient's arteries, which may have been open sufficiently while at rest, provide inadequate blood flow during exercise. The degree of dysfunction after a heart attack has occurred may also be determined to develop a prognosis. For example, patients with serious residual dysfunction after a heart attack are at a higher risk of dying in the first year and more aggressive treatment may be indicated.

As noted above, one of the preferred methods to detect and evaluate regional dysfunction in the left ventricle is to measure the range of wall motion, i.e., the range of movement of the ventricular wall during a cardiac cycle. Another approach is to measure regional wall thickening, which is also an indication of coronary disease and muscle dysfunction. Previous techniques for measuring these parameters have typically relied upon two-dimensional imaging of the cardiac wall, which can introduce significant error due to failure to compensate for the angle of the beam relative to the cardiac wall. In addition, two-dimensional imaging generally is limited in its ability to clearly localize regional left ventricular dysfunction or provide an overall view of an affected region that allows a physician to immediately interpret the extent and degree of dysfunction. Prior art attempts to model the heart in three-dimensional views have not been entirely successful, because such attempts have been based on spherical or helical coordinate systems that can not accurately determine minimum wall thickness in a specific region. Such coordinate system based attempts may be unsuitable in patients whose hearts are distorted by disease. Furthermore, prior art three-dimensional imaging and modeling techniques have been limited to the left ventricle, which tends to be more regular and consistent in size and shape in different patients; in contrast, other portions of the heart exhibit greater variation in size and shape that has precluded referential modeling of such portions for comparison to the corresponding portion of normal, undiseased hearts. Accordingly, it will be evident that a new approach to monitoring cardiac parameters, such as range of wall motion and wall thickening, is needed that is more reliable and provides greater resolution and accuracy in identifying problem regions in the heart.

More importantly, it would be desirable to achieve the improved measurement of such cardiac parameters in real time, so that the technique can be employed during open heart surgery to continuously evaluate the condition of a patient's heart and the effect of anesthesia on the patient. An optimum device for imaging selected portions of the heart is a transesophageal ultrasonic probe. With an imaging probe disposed in the esophagus behind the heart, most of the heart structure can be imaged without interference from the lungs or ribs, as often occurs with transcutaneous imaging. If the patient is anaesthetized during the procedure, there is no discomfort and the probe can be maintained at the same position for several hours. A method for using the image provided by such a probe to model a selected region of the heart so as to determine range of cardiac wall motion and wall thickness at specific points on the cardiac wall in real time will therefore be of significant benefit during cardiac surgery. Furthermore, a method that references specific regions of the heart to a standard or average cardiac template so as to provide a specific identification of an affected region that is generally independent of the size and shape of a patient's heart (even if abnormal due to disease) should aid in better assessing problems that are diagnosed.

SUMMARY OF THE INVENTION

In accordance with the present invention, a method is defined for analyzing characteristic cardiac parameters of a patient's heart. The method includes the step of first imaging a heart to produce imaging data. Using the imaging data, the heart is modeled, producing modeling data corresponding to an inner surface and an outer surface of the heart. The modeling data are preferably produced for a plurality of times during a cardiac cycle, including at an end systole and at an end diastole. A mesh of connected polygons is created that represents the inner surface of the heart. The polygons include a plurality of connected edges that meet at vertices of the polygons. In the next step of the method, a normal for a face of each of the polygons is determined. Next a vertex normal for each of the vertices is determined by averaging the normals for the faces of the polygons that meet at the vertices. The vertex normals are extended as a plurality of line segments that intersect the outer surface at a plurality of points. The line segments thus extend between the vertices of the polygons on the inner surface and the points of intersection disposed on the outer surface. A center surface is defined by connecting midpoints of the line segments. More specifically, the center surface is represented by a mesh comprising a plurality of connected polygons with vertices disposed at the midpoints of the line segments. Using the center surface, characteristic cardiac parameters for the heart are determined.

The method further comprises the step of reiteratively adjusting the center surface (i.e., the mesh representing the center surface) before it is used to determine the characteristic cardiac parameters. The adjustment continues until the center surface meets predefined criteria, which indicate that the center surface is substantially centered between the inner and the outer surfaces. The step of reiteratively adjusting comprises several steps that are applied to each vertex of the connected polygons comprising the mesh representing the center surface. In the first of these steps, an average normal is determined for the vertex by averaging normals to the polygons surrounding the vertex. The average is then extended as a test line segment that intersects the inner surface and the outer surface. Next, a first distance between the center surface and one of the inner surface and the outer surface is compared with a total distance between the inner surface and the outer surface. Both the first distance and the total distance are measured along the test line segment. Next, the vertex of the center surface is moved to a midpoint of the test line segment. The center surface as thus adjusted is used for determining cardiac parameters of the heart, but only if a last adjustment of the center surface made has enabled the center surface to meet the predefined criteria. If not, then the steps for adjusting the center surface are repeated. The predefined criteria are met if: (a) the last adjustment of the center surface has not resulted in a connectivity change of the connected polygons extending over the center surface; and, (b) a mean of a ratio of the first distance to the total distance for all of the vertices on the center surface as last adjusted is substantially equal to 0.5.

In the preferred embodiment, the connected polygons comprising both the mesh representing the inner surface and the mesh representing the center surface comprise triangles. In addition, the characteristic cardiac parameters for the heart preferably include at least one of a range of motion for a wall of the heart, and a thickness of the wall of the heart.

The step of imaging the heart includes the steps of digitizing an analog output signal of an imaging device to produce a digital signal. Images of the inner and the outer surfaces of the heart produced using the digital signal are graphically displayed. Borders of the inner and the outer surfaces of the heart on the graphically displayed images are traced to define the imaging data at an end systole and at an end diastole of the cardiac cycle. The center surface is preferably determined using the modeled data for both the end systole and the end diastole.

The method further comprises the step of determining if a fold exists on the center surface. To determine if a fold exists, a check is made to determine if a dihedral angle measured between the faces of adjacent polygons on the center surface that are joined along a common edge is less than a predefined value. If a fold is found to exist, said method further comprises the steps of implementing two steps for each vertex of the polygons comprising the mesh representing the inner surface. First, a smoothing normal is determined for the vertex by averaging the vertex normal of the vertex with the vertex normals of surrounding vertices. Next, the vertex normal of the vertex is replaced with the smoothing normal. After these steps are completed for all of the vertices, the smoothing normals are used as the vertex normals for the mesh representing the inner surface in again determining the mesh representing the center surface.

The method also comprises a similar step of determining if a fold exists in the center surface after the center surface is adjusted. If a fold is found to exist in the center surface after it has been adjusted, a last adjustment to the center surface is undone. Then, for each vertex of the polygons comprising the mesh representing the center surface, a smoothing normal is found by averaging the vertex normal of the vertex with the vertex normal of surrounding vertices. The vertex normal of the vertex is replaced with the smoothing normal. Thereafter, the smoothing normals are used as the vertex normals for the mesh representing the center surface in determining a subsequent adjustment to the center surface.

The step of using the center surface to determine characteristic cardiac parameters for the heart comprises several steps that are implemented for each vertex on the center surface. Specifically, the first of these steps provides for determining a normal to each connected polygon surrounding the vertex. An average vertex normal for the vertex is found by averaging the normal for the polygons surrounding the vertex. The average vertex normals are extended to intersect the inner surface and the outer surface at a plurality of points. By connecting the plurality of points on the inner surface, a plurality of tiled sections are formed on the inner surface. Similarly, by connecting the plurality of points on the outer surface, a plurality of tiled sections are formed on the outer surface. The tiled sections on the inner surface define first ends of volumetric elements that extend through the center surface, between the inner surface and the outer surface, and the tiled sections on the outer surface define second ends of the volumetric elements. A mean area is determined for the first and the second ends of each of the volumetric elements. Likewise, a volume is determined for each of the volumetric elements. As a function of the mean area of the first and second ends and the volume of said volumetric elements, a thickness of the cardiac wall is found at each of the volumetric elements.

In addition, the method further includes the step of determining a thickening of the cardiac wall at a volumetric element during the cardiac cycle. To determine the thickening, a difference between the thickness of the cardiac wall at the volumetric element at an end diastole and an end systole of the cardiac cycle is found. To determine the thickening, the center surfaces at the end systole and at the end diastole are determined and are employed to find the volumetric elements at end systole and at end diastole. By comparison of the volumetric elements at end systole and at end diastole, changes in the thickness of the cardiac wall (i.e., thickening) are determined.

Another aspect of the present invention is directed to a method for determining a center surface that is centered between a first surface and a second surface modeled to represent a cardiac wall of a patient's heart, for use in analyzing characteristic cardiac parameters. This method includes steps that are generally consistent with the steps of the method described above.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 27 is a flow chart of the steps employed in determining regional wall motion;

DETAILED DESCRIPTION OF THE PREFERRED EMBODIMENT OVERVIEW OF THE METHOD FOR DETERMINING CARDIAC PARAMETERS

Figure 1:
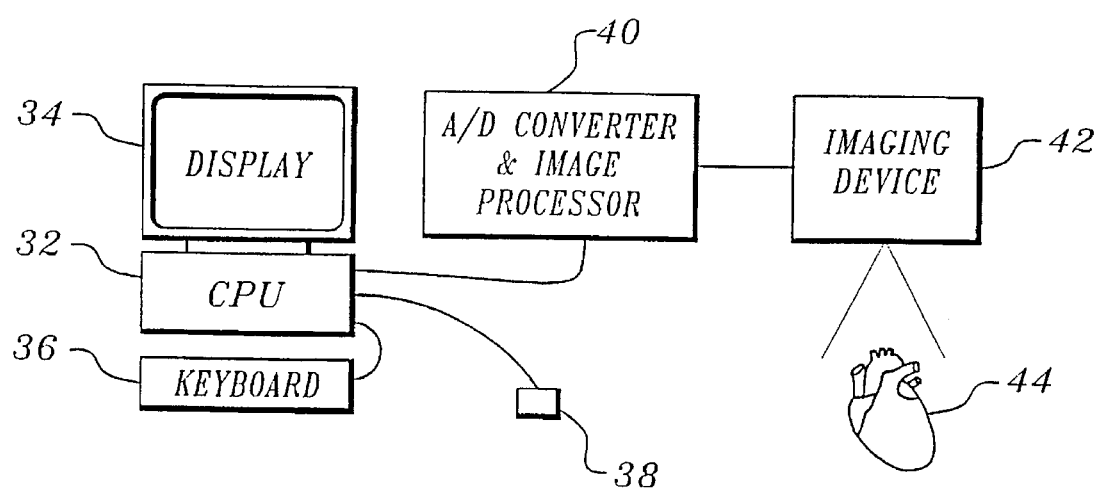
FIG. 1 is a schematic block diagram of a system in accordance with the present invention that is used for determining cardiac parameters, including thickness of the cardiac wall and range of motion during a cardiac cycle.

A cardiac imaging and model processing system 30 is disclosed in FIG. 1. This system includes a central processing unit (CPU)32 (personal computer or graphic workstation terminal) that is coupled to a graphics display 34, and to a keyboard 36 for input of data or instructions controlling the image processing and modeling procedures used to determine cardiac parameters in accordance with the present invention. In addition, a mouse 38 (or other cursor pointing device) is coupled to CPU 32 for use in graphically controlling software running on CPU 32, for example, by selection of menu items, or for manually tracing images produced on graphics display 34, as explained below.

CPU 32 is coupled through an appropriate input card or port (neither shown) to an analog-to-digital converter (ADC) and image processor 40. ADC and image processor 40 receives an analog signal produced by an imaging device 42, converts the analog signal to a digital signal, and processes the digital signal to a form appropriate for input to CPU 32 and display on graphics display 34. In addition, ADC and image processor 40 controls the imaging device as it scans a heart 44 beating inside a patient (not shown). Details of the processing are not included, since they depend on the type of imaging device used and are well known in the art. For example, it is contemplated that imaging device 42 may comprise an ultrasound probe, a magnetic resonance imaging system, or a cine CT imaging system, all of which are well known to those of ordinary skill in this art. Although each of these types of imaging devices could provide the analog signal used to create an image of heart 44 on graphics display 34, the current preferred form of cardiac imaging and model processing system 30 uses ultrasound for imaging heart 44.

Figure 2A:
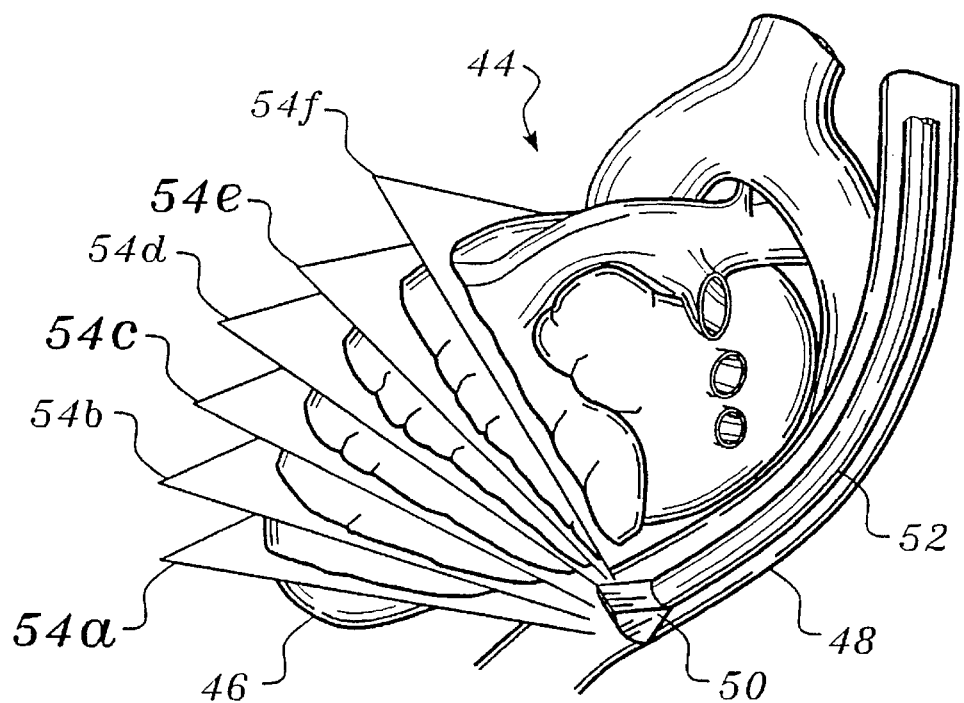
FIG. 2A is an isometric schematic view of a heart and a portion of an esophagus, illustrating how a transesophageal ultrasonic probe is used to image the heart.

Specifically, as shown in FIG. 2A, a transesophageal ultrasonic probe 50 is the preferred form of imaging device 42. This probe is schematically illustrated in a position adjacent heart 44, where it has been inserted through a patient's esophagus 48. The transesophageal ultrasonic probe is coupled to ADC and image processor 40 through a cable 52, which extends upwardly through the esophagus and out of the patient's mouth (not shown). Since esophagus 48 extends downwardly toward the stomach (not shown) at the back side of the heart, the transesophageal ultrasonic probe can readily be located within the esophagus or stomach, in an ideal position to ultrasonically scan at least a selected portion of heart 44, and in the illustrated example, is positioned to scan a left ventricle 46 of the heart.

At this point, it should be emphasized that although the preferred embodiment of the present invention is disclosed in connection with determining cardiac parameters of left ventricle 46, it is equally applicable and useful in determining cardiac parameters for other portions of the heart. In particular, because of a referential mapping scheme employed that relates the determination of cardiac parameters to anatomical landmarks in the heart, it can be used to determine cardiac parameters of portions of the heart that vary significantly from patient to patient, both in size and shape, unlike prior art techniques for forming three-dimensional models of the heart. It should also be noted that a design for transesophageal ultrasonic probe 50 has been developed that is particularly useful for scanning the heart to produce imaging data used in the present invention; however, details of the design of this probe are not disclosed herein, since they do not directly relate to the present invention. A more conventional ultrasonic probe can also be used for this purpose, including one operated transcutaneously, as long as the location and orientation of the probe can be recorded for each imaging plane.

Figure 2B:
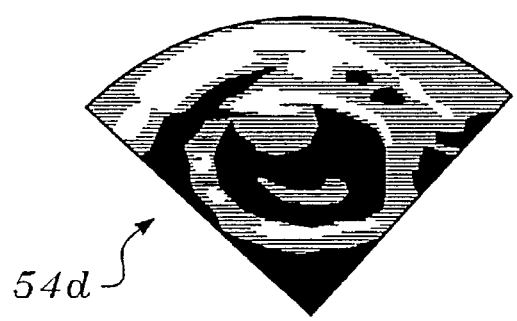
FIG. 2B is a graphic representation of one of the image planes produced by the transesophageal ultrasonic probe.

In the position shown in FIG. 2A, transesophageal ultrasonic probe 50 produces a plurality of images along planes 54a through 54f. An exemplary image along plane 54d is illustrated in FIG. 2B as it would appear on graphics display 34 (shown in FIG. 1). In effect, each image plane represents a cross-sectional scan of left ventricle 46, showing the various anatomical landmarks of the heart and both the inner and outer surfaces of the left ventricle in the particular plane of the scan. Ideally, ultrasonic scans should be made of heart 44 from a plurality of different positions.

Figure 3:
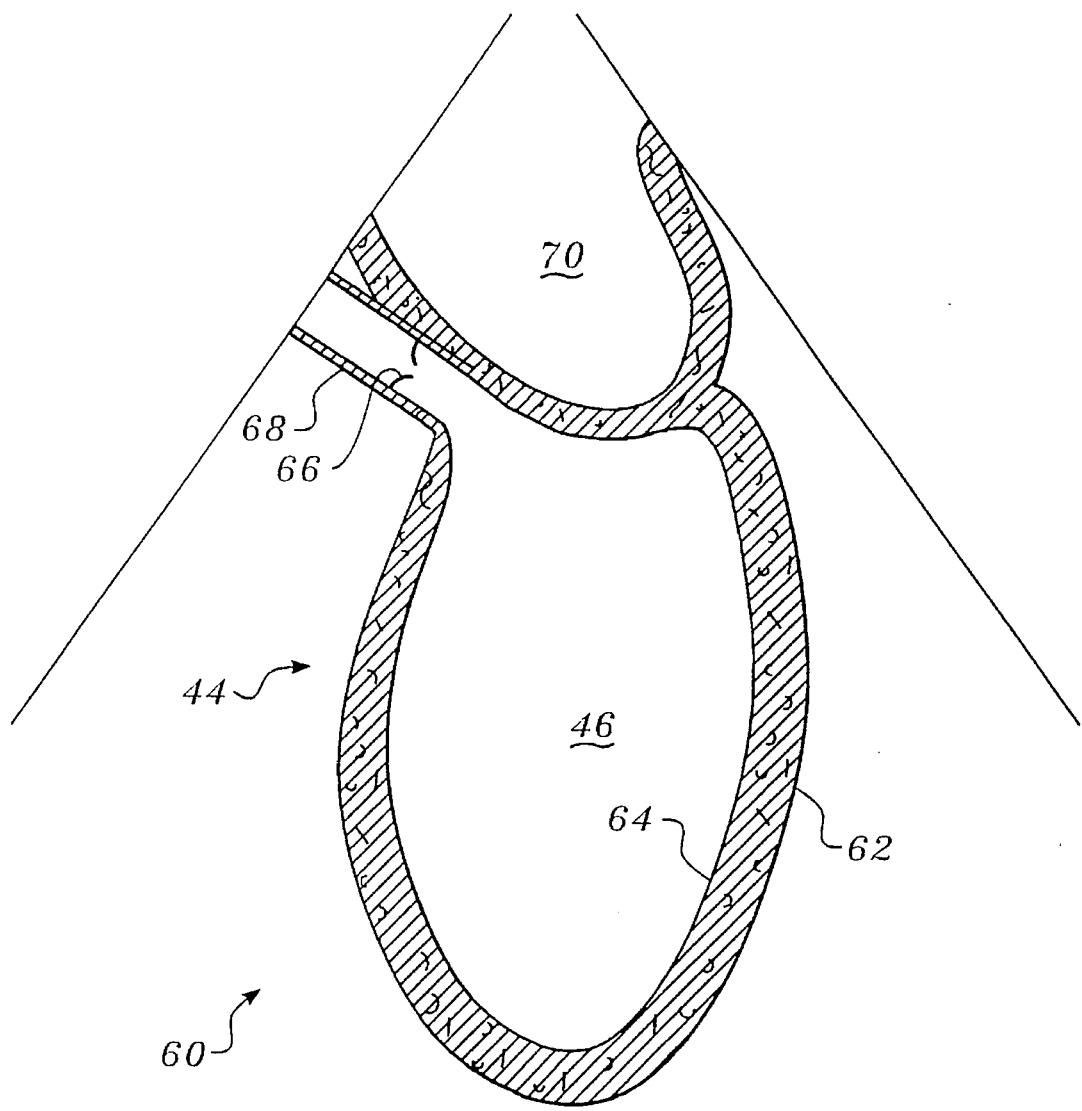
FIG. 3 illustrates a schematic cross-sectional view of a portion of the heart imaged along its longitudinal axis, through the left ventricle.

FIG. 3 shows a schematic representation 60 of an ultrasonic imaging system scan made along the longitudinal axis of heart 44, principally focusing on left ventricle 46. An outer surface 62 (medically referred to as the epicardial surface) is clearly visible, as is an inner surface 64 (medically referred to as the endocardial surface). Also indicated in the longitudinal axis view of FIG. 3 is an aortic valve 66 at the mouth of an aorta 68. A portion of a left atrium 70 is visible in the upper portion of the ultrasonic scan image.

Figure 4:
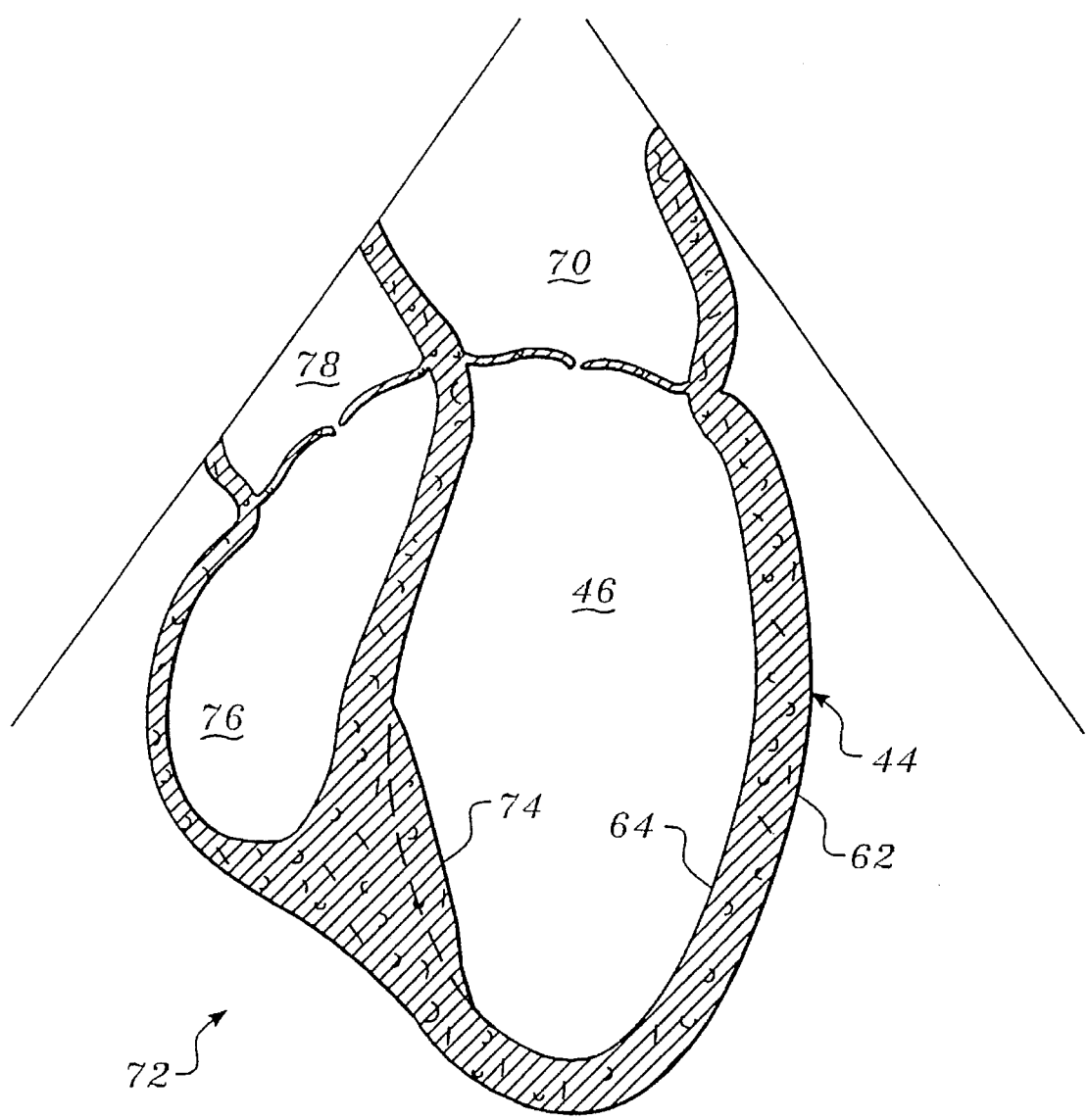
FIG. 4 is a schematic cross-sectional view of a portion of the heart imaged through the chambers of the heart.

By moving the transesophageal ultrasonic probe to a different position, a chamber image view 72 as schematically illustrated in FIG. 4 is produced. In this view, a portion of a right ventricle 76 and a right atrium 78 are visible, as well as a papillary muscle 74.

Figure 5:
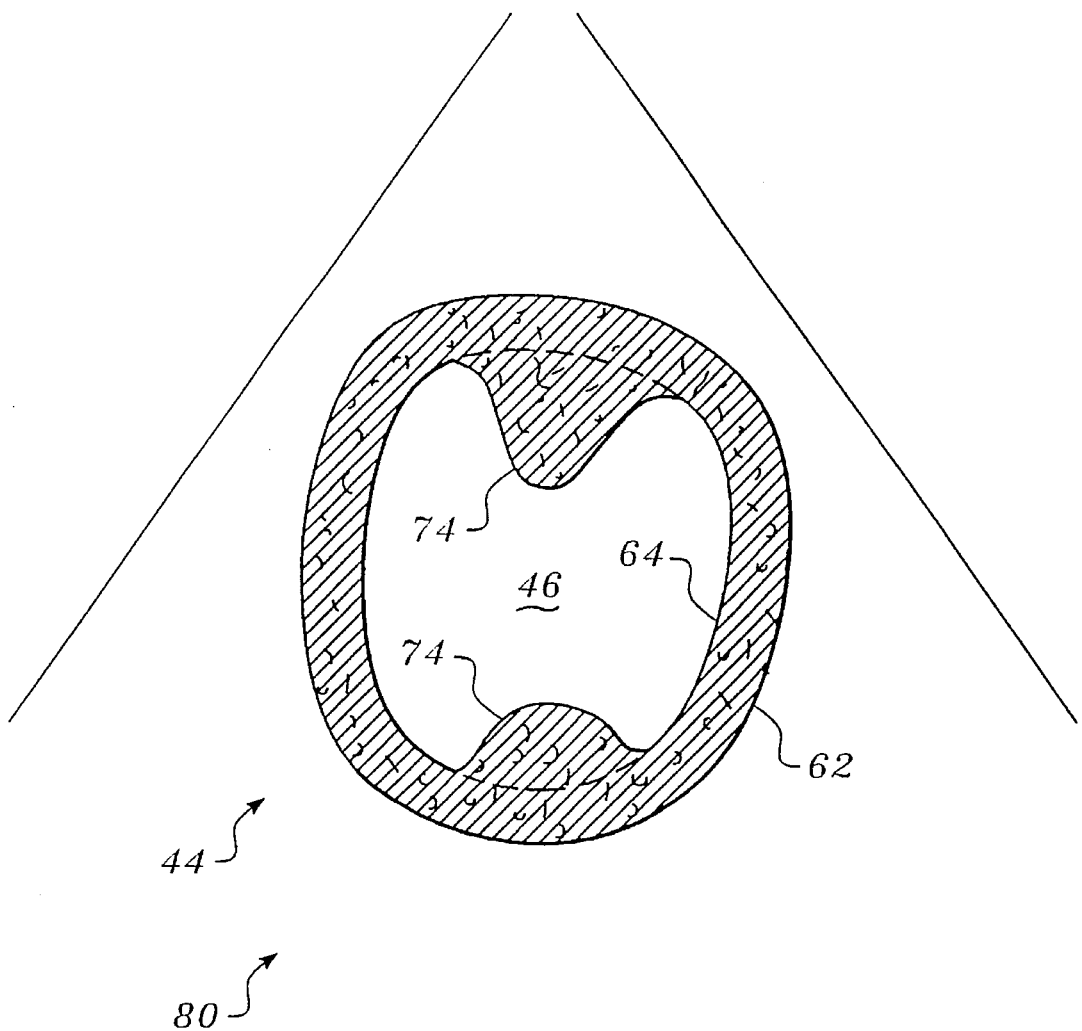
FIG. 5 is a schematic cross-sectional view of the left ventricle, imaged along a transverse axis.

Finally, a transverse or short axis view image 80 of left ventricle 46 is shown in FIG. 5. In this Figure, the intrusion of papillary muscle 74 into the chamber of left ventricle 46 is more clearly evident.

The images produced by imaging device 42 can be stored for later processing by CPU 32 on any appropriate non-volatile storage device, such as an analog disk or video tape. Alternatively, the digital data provided by ADC and image processor 40 can be conveyed over a local or wide area network to CPU 32 for display on graphics display 34, or can be stored on a hard drive or on digital tape associated with the CPU, for subsequent processing.

Figure 6A:
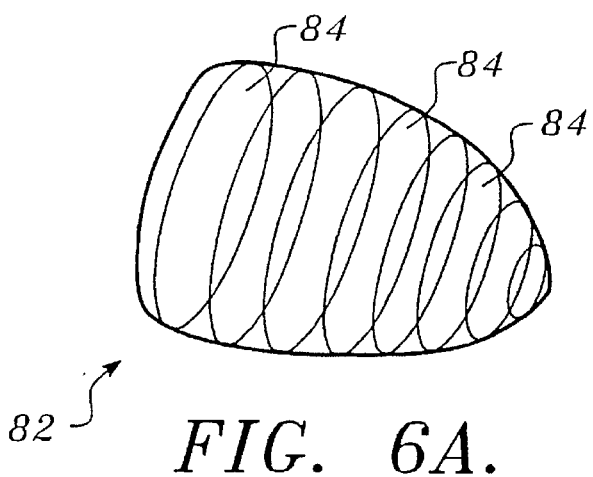
FIGS. 6A and 6B schematically illustrate the cross-sectional images planes that are in parallel with the transverse axis of the heart and those that are orthogonal thereto, in parallel with the longitudinal axis, as produced by a magnetic resonance imaging system.
Figure 6B:
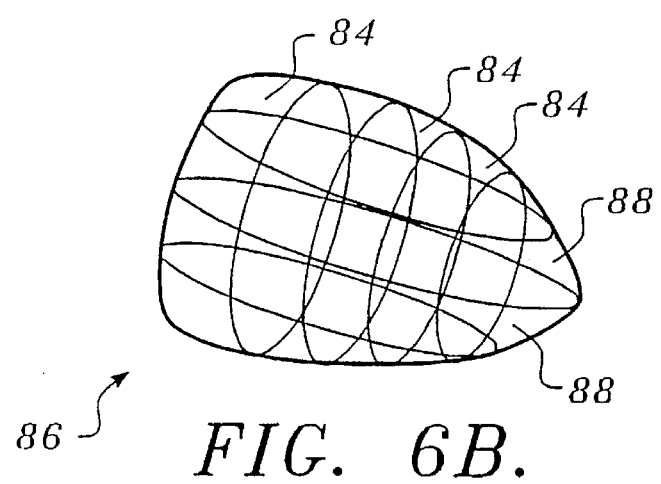

FIGS. 6A and 6B disclose the image planes of the left ventricle used to produce the imaging data with a magnetic resonance imaging system. A magnetic resonance system provides image data 82 for at least eight planes 84 that are transverse to the longitudinal axis, i.e., parallel to the transverse axis of the left ventricle. In addition, imaging is also carried out in an orthogonal direction to produce imaging data 86, along four planes 88 that are parallel to the longitudinal axis. The imaging data represented in FIG. 6B is obtained sixteen times during the cardiac cycle so that each frame of eight transverse and four longitudinal image planes are secured at intervals separated in time by about 33 milliseconds. The peak of the R-wave on an electrocardiogram (ECG) (not shown) is used to trigger the imaging system for each cardiac cycle.

Figure 7:
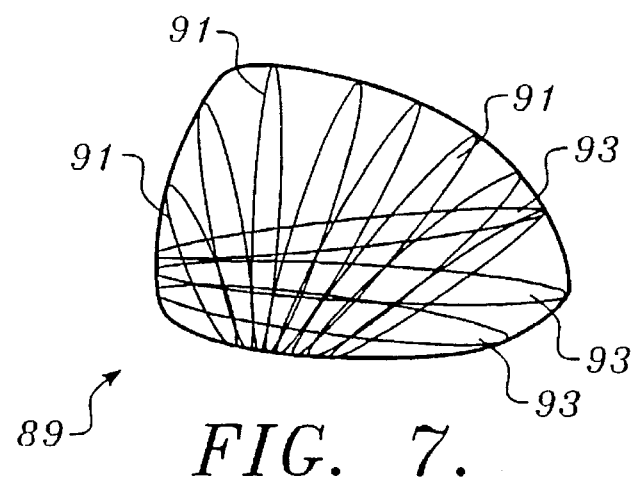
FIG. 7 illustrates the angulated cross-sectional image planes obtained with an ultrasonic imaging probe, from two different imaging positions.

As shown in FIG. 7, the imaging planes developed by using transesophageal probe 50 include a plurality of angulated planes 91 scanned when the esophageal probe is disposed in one position, and a plurality of angulated planes 93 scanned when the esophageal probe is in a different position. An appropriate coordinate transformation is used in connection with this imaging data when each image plane is traced on graphics display 34 to compensate for the different imaging positions of the probe and for the fact that the image planes are not parallel to each other or orthogonal.

Once an image along one of the planes scanned by imaging device 42 is visually represented on graphics display 34, an operator can manually outline or trace the borders of the left ventricle endocardium and epicardium using mouse 38. When manually outlining these surfaces on a given image plane, borders corresponding to specific anatomic structures within heart 44 are input by tracing to define landmarks or reference points. These anatomic structures include papillary muscles 74, the interventricular septum (not separately shown) and various valves, such as aortic valve 66. For tracing of the left ventricle, the mitral valve structure (not shown) will be included in detail, as an additional reference landmark.

The image planes developed by imaging device 42 will typically be scanned over several cardiac cycles. During at least one cardiac cycle, an end diastole and an end systole will be selected for each of the image planes. The end diastole frames represent the left ventricle at the time of the greatest chamber area, and similarly, the image planes at end systole will be selected to represent the left ventricle when it has the smallest chamber area. To determine which image planes were scanned at a particular time during the cardiac cycle, an ECG and/or a phonocardiogram will be recorded during the imaging process, providing cardiac cycle data corresponding to each of the image planes scanned that identify the particular time in the cardiac cycle in which the image plane was produced. The endocardial and epicardial borders that are manually traced are stored as x-y coordinates, representing a series of points defining the inner and outer surface of the heart and the referential landmarks during each image plane visualization. Since the left ventricular contours on angiograms are traced at the outer limits of the intertrabecular crevices, visualized as wispy streaks of contrast, the endocardial border and ultrasound-produced images will be traced at the outermost edge of the blood-myocardium interface.

It is also contemplated that the manual tracing of these image plane visualizations can alternatively be accomplished by software running on CPU 32 without human intervention. In other words, the current manual tracing step will be replaced by a computer automated procedure to obtain equivalent border-traced data points using software that responds to differences in contrast and shading in the graphics image to recognize borders of the endocardial and epicardial surfaces and anatomical structures that should be included in the traced data. The automated tracing of the image plane visualization will be required to accomplish determination of cardiac parameters in real time.

The traced borders and referenced cardiac structure landmarks in the heart represent data that are stored in a database, together with header information identifying the patient and the location and orientation of the imaging plane for which the data were developed. Once all of the images developed by scanning the heart of the patient have been traced, the borders developed by the manual (or automated) tracing procedure are output from the database as x, y, and z coordinates, the z coordinate depending upon the spatial position of the particular image plane that was traced to produce the series of data points defining the borders of the surfaces of the heart and its anatomical landmark structures.

The data developed by tracing the surfaces of the heart represented by the image planes are then assembled and used to prepare a three-dimensional reconstruction of the left ventricle surfaces. Details of this reconstruction or modeling of the left ventricle surfaces are disclosed below.

In order to reconstruct the endocardial left ventricle surface, a coordinate grid of the longitudinal and cross-sectional interpolated borders is sorted into sets of three points to define the corners of triangular tiles. At any point where two borders cross without intersecting, the border with better spatial resolution is considered as the more accurate.

The above-disclosed method is used to construct a model having an epicardial surface and an endocardial surface at end diastole and at end systole, for use in determining wall thickening. In addition, a model of the endocardial surface at end diastole and end systole, representing the location of the endocardial surface at the two extreme chamber volume conditions during a cardiac cycle is created using the data developed for each image plane at the end diastole and end systole times during the cardiac cycle. The second model is used in determining the range of motion for different portions of the left ventricle, as explained below.

Determination of these two cardiac parameters first requires that a center surface be defined between the inner and outer surfaces of each model, i.e., a center surface must be determined between the epicardial and endocardial surfaces, and a center surface must be determined between the endocardial surfaces at end diastole and end systole and between the epicardial surfaces at end diastole and end systole. Substantially the same technique is used to develop the center surface for both models.

Figure 8:
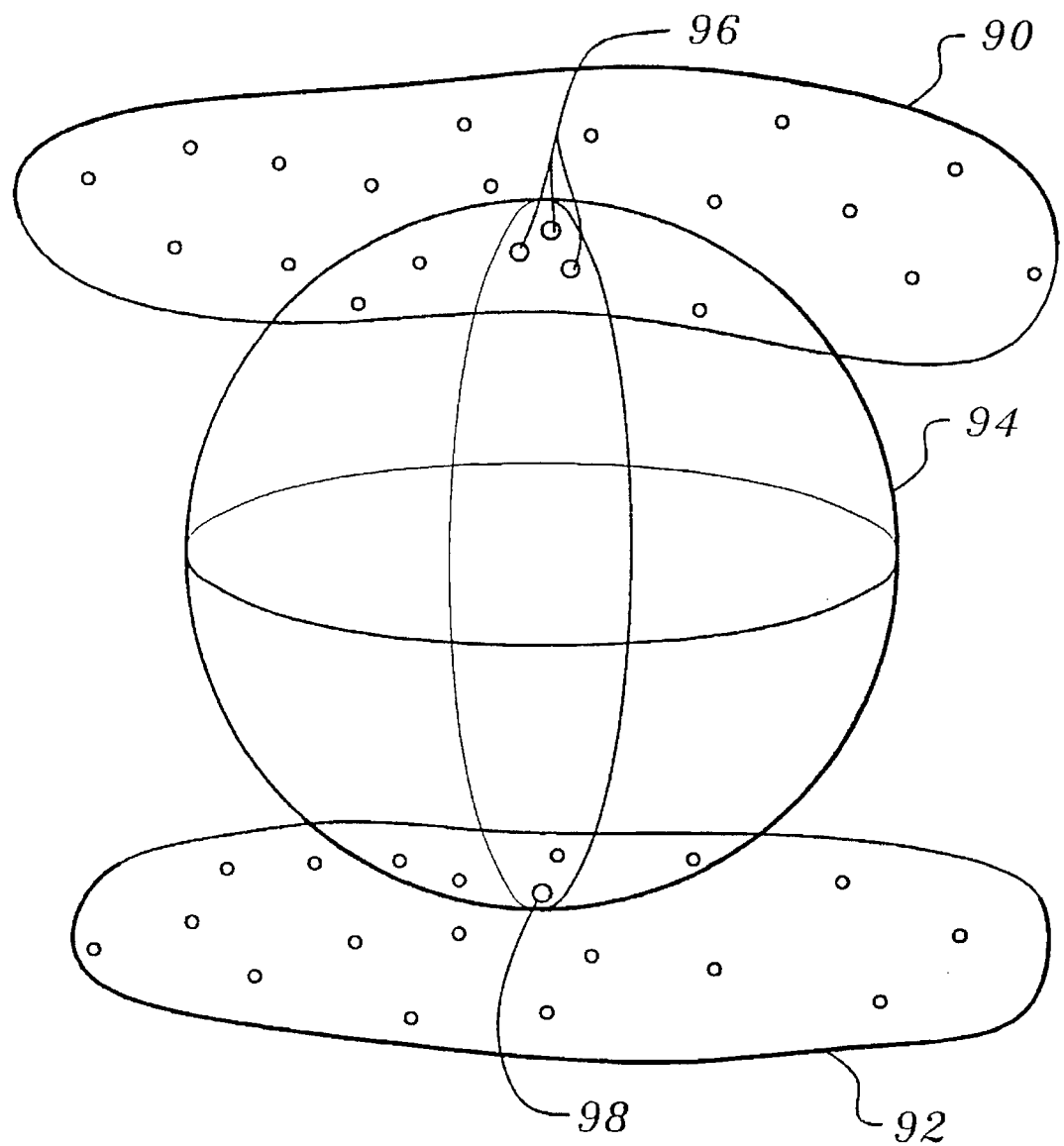
FIG. 8 is an exemplary schematic representation of one of a plurality of spheres that are produced to fill a space between two modeled surfaces of the left ventricle, in a first embodiment of the method used to define a center surface.

Three approaches can be used for defining the center surface between the inner and outer surface of a model of the left ventricle. In the first approach, which is illustrated in an exemplary manner in FIG. 8, a space between the inner and outer surface, in this case represented by an end diastolic endocardial surface 90 and an end systolic endocardial surface 92, is filled with a plurality of spheres (like a sphere 94) that meet certain requirements. Although only a single sphere 94 is shown in FIG. 8, it will be understood that many such spheres fill the space between the two surfaces of the model. Each sphere 94 must touch four points on the inner and outer surfaces, including at least one point on each of the inner and outer surfaces, and must enclose no other points. The centers of all spheres 94 are then interconnected with lines (not shown) that define the center surface.

Figure 9:
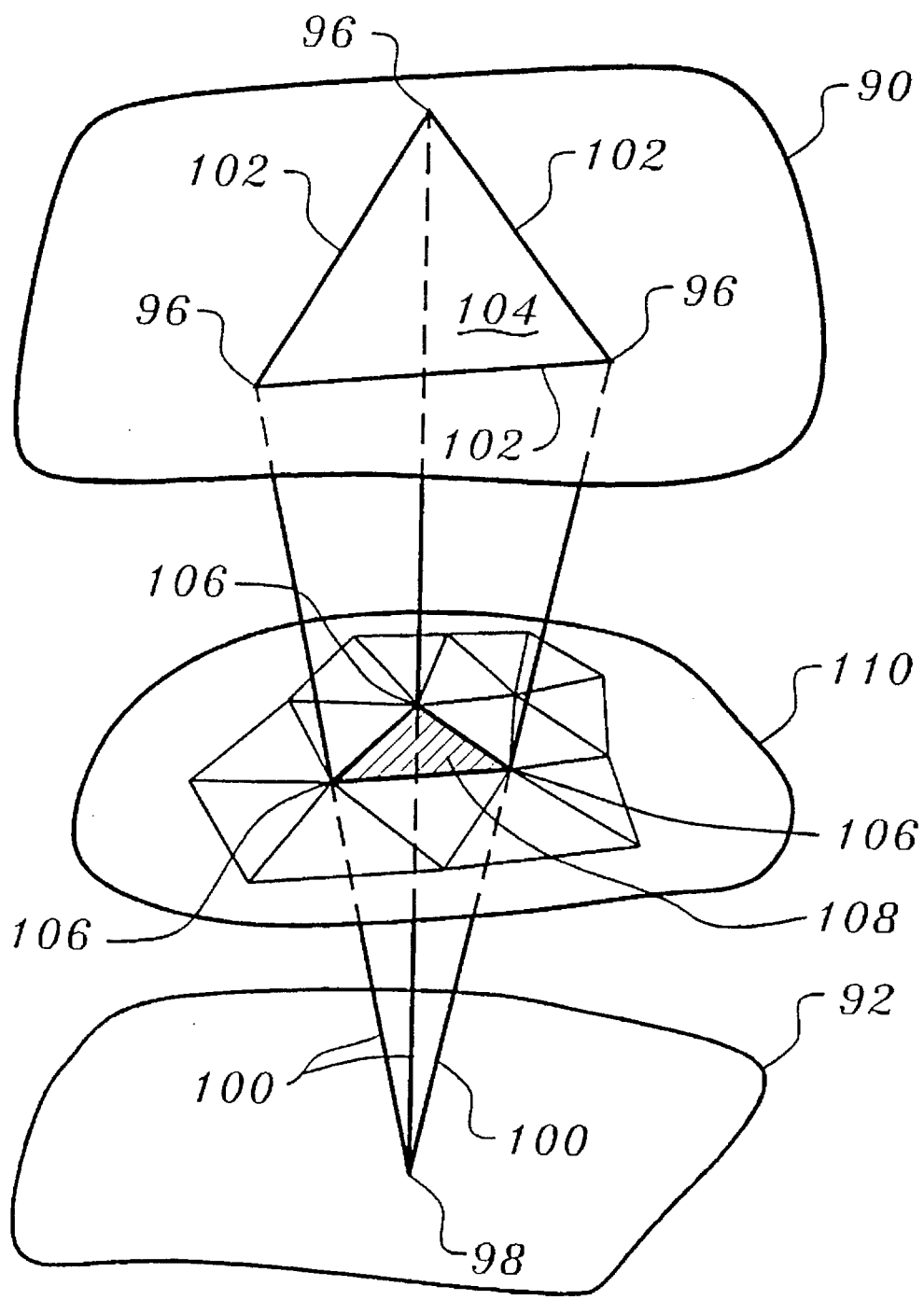
FIG. 9 illustrates the use of tetrahedrons to define a center surface between two surfaces of the left ventricle, in a second embodiment of the method.

The second method for defining the center surface is generally illustrated in FIG. 9. In this approach, a plurality of tetrahedrons is defined by connecting points 96 on end diastole endocardium surface 90 to a point 98 on end systole endocardium surface 92 with lines 100. Points 96 are connected with lines 102 to form a triangular patch 104, which is similar to a triangular patch 108 formed by connecting midpoints 106 of lines 100 together. A series of such triangular patches 108 thus define a center surface 110.

Figure 35:
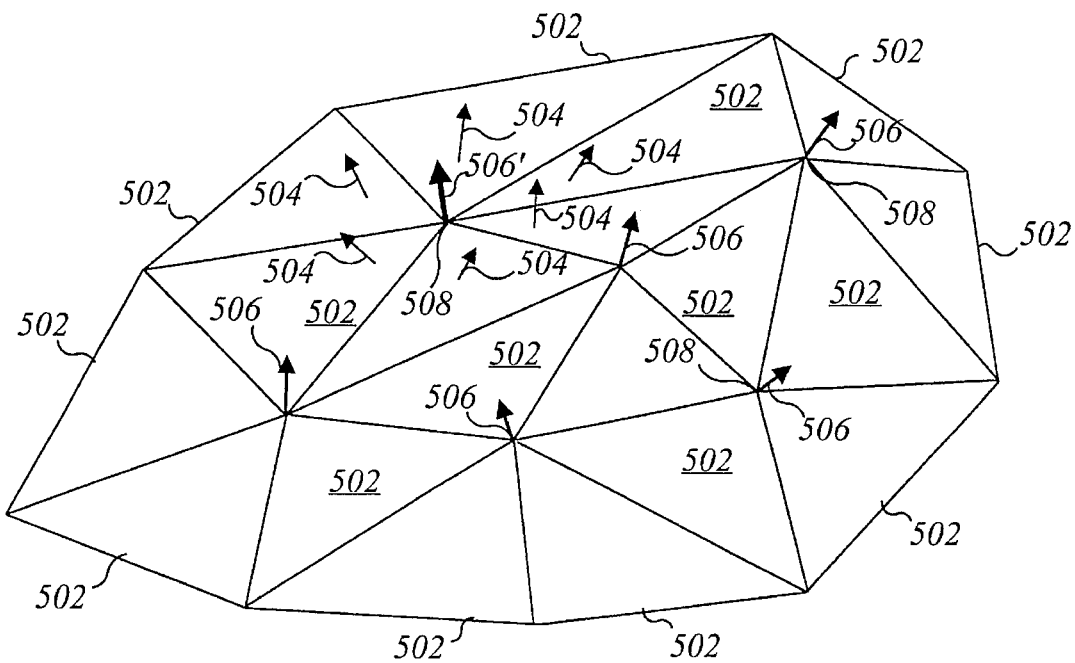
FIG. 35 illustrates a mesh of connected triangles on a small portion of a modeled inner surface of a heart.

A third method for defining the center surface begins by creating a mesh 500 of connected triangles 502 that represents the inner surface of the heart, a small portion of which is illustrated in FIG. 35. The mesh comprising the connected triangles is similar to the tiled surface of triangular patches discussed above; however, slightly different terminology is used in describing the third method to more clearly distinguish it from the first two methods for defining the center surface. In the mesh representing the inner surface, adjacent triangles share common edges and include vertices 508 that are disposed at each end of an edge. A (geometric) normal 504 exists relative to the face of each triangle 502. The directions in which the normals extend from the triangle faces are defined by applying the "right-hand rule" to the direction traversed about the edges defining the face of each triangle 502. The right-hand rule is a simplistic precept typically used to determine the direction of a vector that is the cross product of two other vectors. The rule is applied in the present case as follows. A triangle comprising the mesh representing the inner surface is viewed from the modeled outer surface (i.e., viewed from the outside looking in); the edges of the triangle are then traversed in a direction corresponding to that in which the fingers of the right hand naturally curl toward the palm. The upwardly pointing thumb of the right hand will point in the direction of the normal or vector that is perpendicular to the face of the triangle. The normals are thus determined for each triangle face comprising the mesh representing the inner surface and are standardized to a length of one.

For each vertex of this mesh, all of the normals of triangles meeting at the vertex (i.e., the "common vertex") are averaged to determine a vertex normal 506 for the common vertex. For example, in FIG. 35, a vertex normal 506' is determined by averaging normals 504 to the faces of all of the triangles surrounding the common vertex. This process is repeated for all of the vertices of the triangles comprising the mesh representing the inner surface.

Figure 36:
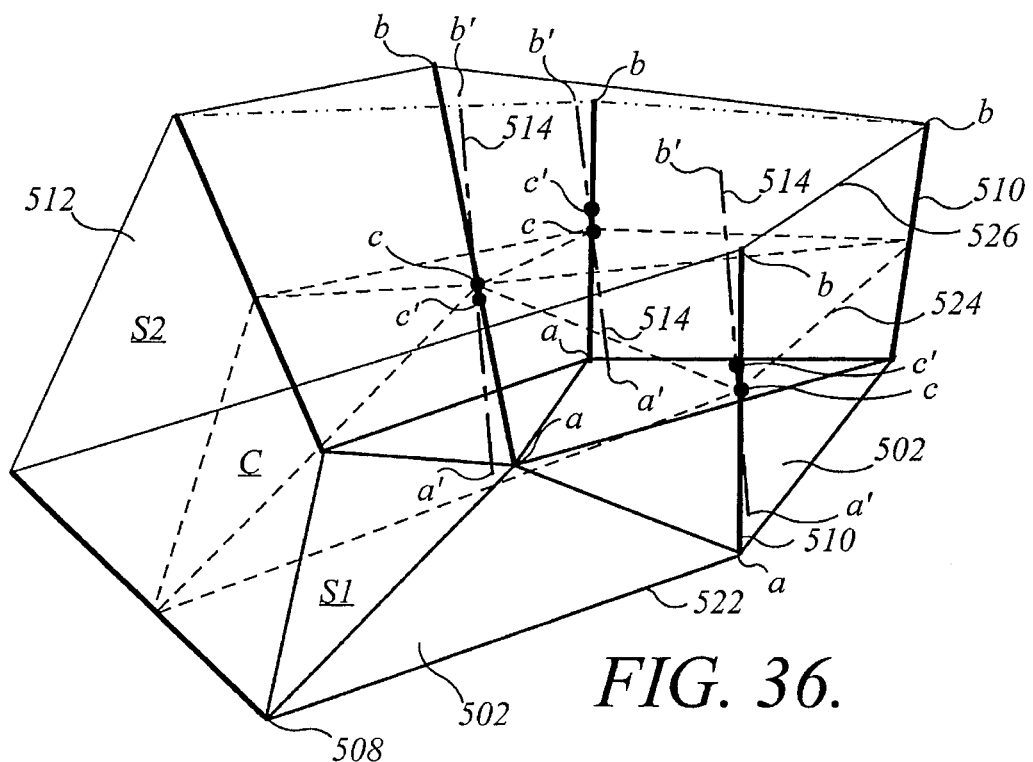
FIG. 36 illustrates the center surface determined by midpoints of line segments extending along vertex normals of a mesh on the inner surface, to a modeled outer surface, and illustrates how the center surface is adjusted to minimize its error.

Vertex normals 506 of the triangles comprising mesh 500 are then extended to form line segments 510 that intersect the outer surface, as shown in FIG. 36. An initial or candidate center surface 524 is determined by connecting the midpoints of the line segments to form a plurality of connected triangles comprising a second mesh, C, which represents the center surface, and the connected triangles in mesh C generally correspond to the triangles comprising the mesh representing the inner surface. However, the mesh representing the initial or candidate center surface will likely require an update or adjustment to reduce errors in its position between the inner and outer surfaces. Accordingly, the mesh representing the center surface is reiteratively adjusted until it meets predefined convergence criteria. The finally adjusted center surface is then output for use in determining cardiac parameters, as discussed further below.

Figure 10:
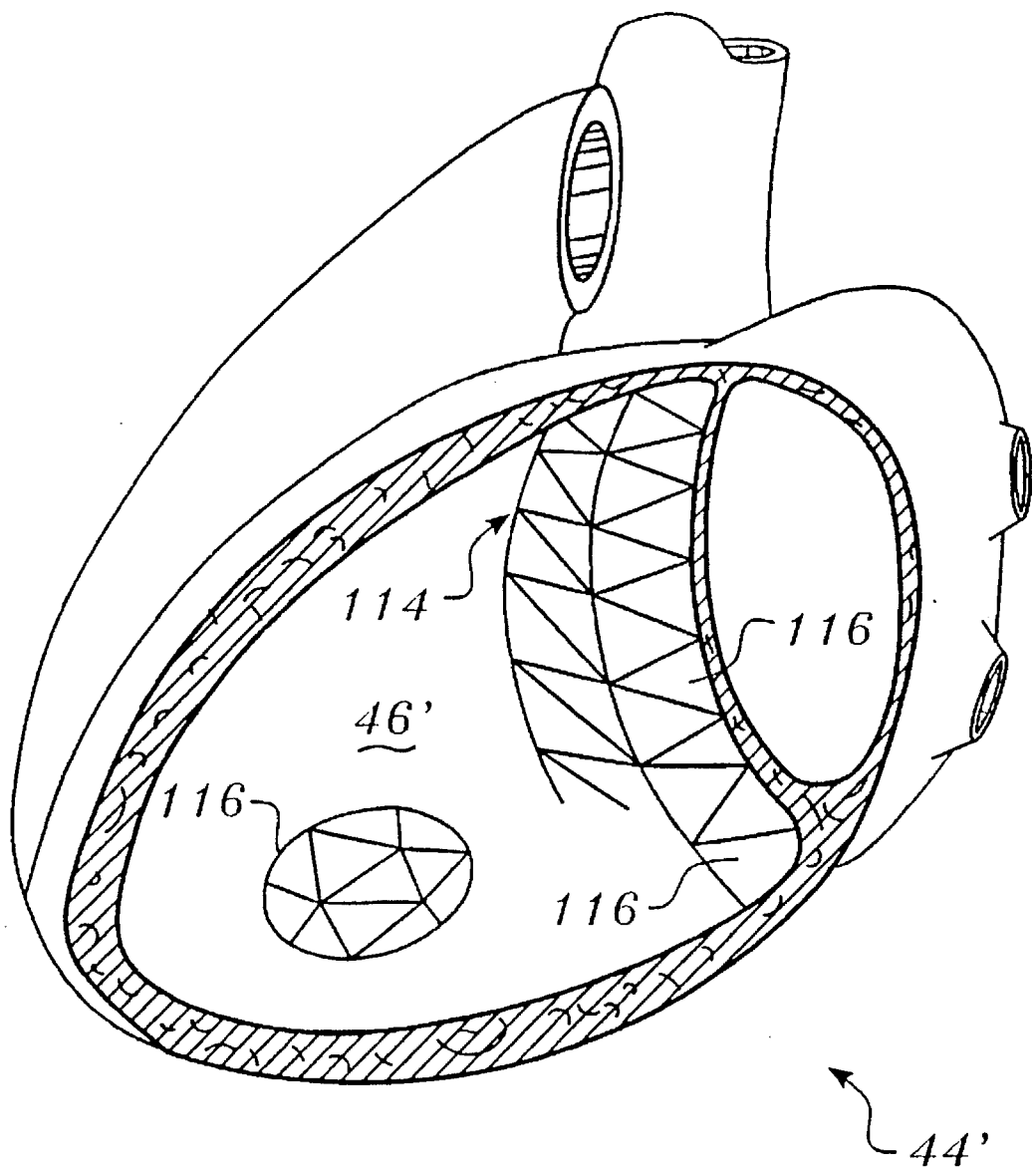
FIG. 10 illustrates a few of the triangular tiled sections representing an average center surface template that is mapped onto the center surface of a specific patient's heart.

There are two techniques for referencing the tiles or connected triangles representing the center surface to the anatomic landmarks in the heart, such as the mitral valve and papillary muscles. In the first technique, which is applicable to the first two methods for defining the center surface discussed above, an average center surface template 114 (FIG. 10) is developed by determining a center surface for each of a number of left ventricles of people having a range of left ventricles of different sizes and shapes. This average center surface template comprises a plurality of triangular tiled sections 116, each of which has a specific identifying number associated with it. Furthermore, the average center surface template is referenced to the anatomic reference landmarks in the heart, such as the mitral valve and papillary muscles.

Having defined the center surface for the left ventricle of the heart of the patient using one of the first two methods, this average center surface template 114 is mapped onto the center surface of the patient's heart using the referenced landmarks in the patient's heart to locate the average center surface template. This mapping operation may result in a distortion of the triangular tiled sections 116 as they are mapped onto the center surface of the patient's heart, due to differences in the size and shape of the left ventricle in the patient, compared to the average center surface template. However, since each of the triangular tiled sections are identified and located in respect to the referential landmarks, the mapping operation provides a basis for identifying specific locations in the left ventricle during diagnostic analysis of the cardiac parameters defined using the center surface.

Figure 11:
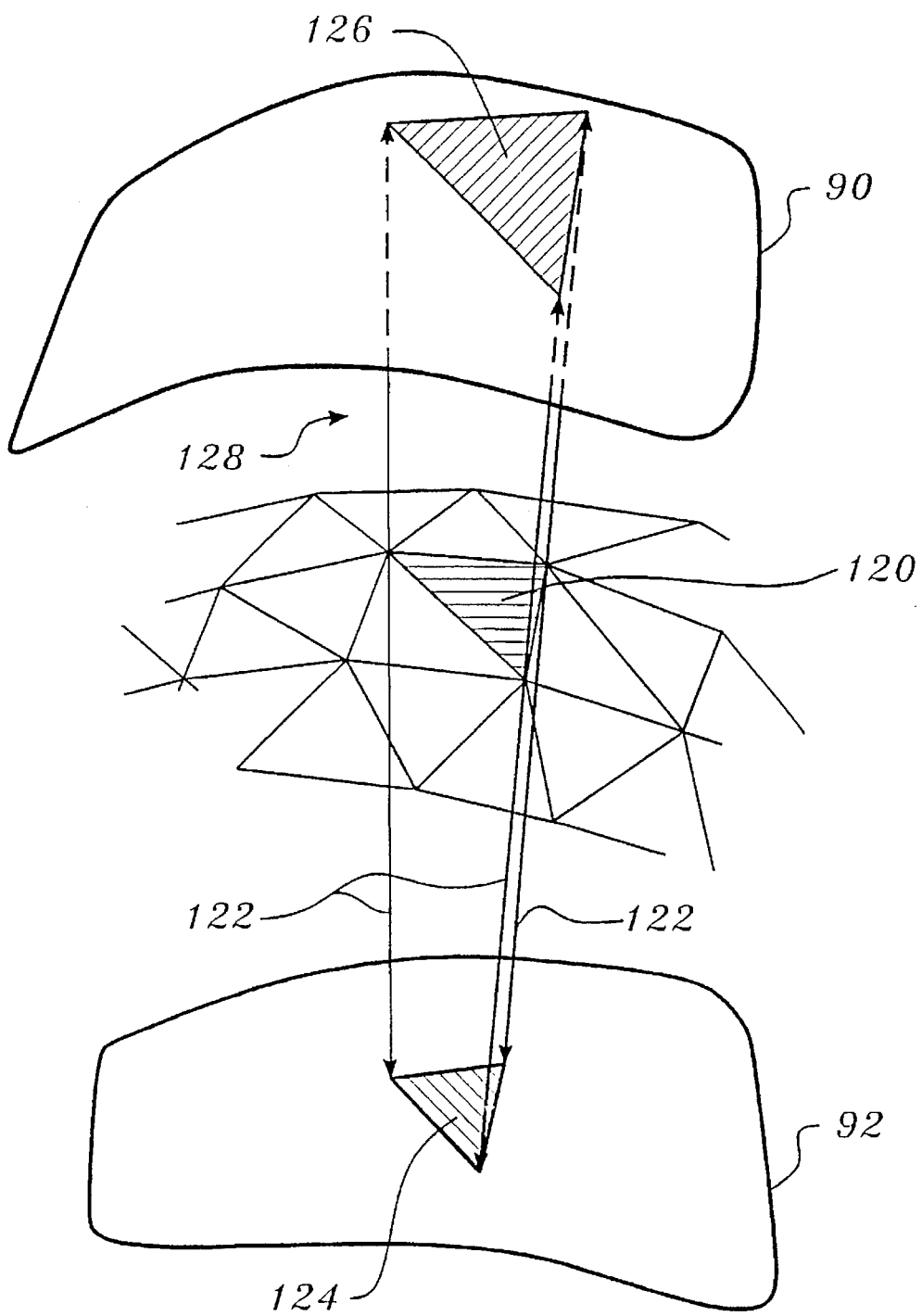
FIG. 11 illustrates how the tiled sections mapped onto the center surface are projected onto the inner and outer surfaces representing the endocardium at end systole and end diastoles; respectively, to define one of a plurality of triangular prisms used to determine range of motion.

The next step involves the projection of the triangular filed sections 120 produced by mapping the average center surface template onto the patient's center surface to produce corresponding triangular tiled sections 120 on the outer surface that was modeled. The projection of triangular tiled section 120 onto the outer surface as shown in FIG. 11 produces a corresponding triangular tiled patch on the modeled left ventricular endocardium at end diastole. Similarly, the projection of the triangular tiled section onto the inner surface of the model produces a corresponding triangular tiled section 124 on the modeled left ventricular endocardium at end systole. In projecting each triangular tiled section 120 onto these inner and outer surfaces of the model, lines 122 are extended perpendicular to an average plane (not shown) through the common junction of each of a plurality of the triangular tiled sections 120. The orientation of the average plane is determined by summing unit vectors that are normal to each of the tiled sections around a vertex of triangular tiled section 120, thereby determining a normal to the average plane, i.e., the direction of the line 122 at that vertex. The points at which lines 122 intersect the inner and outer surfaces of the model thus define the size and shape of triangular tiled section 124 and 126, respectively. Since the directions of lines 122 are determined relative to the average plane, triangular tiled sections 124 and 126 do not overlap with any other triangular tiled sections on these modeled surfaces.

Triangular tiled sections 124 and 126 comprise the ends of a triangular prism 128 that defines a volumetric element. A plurality of such volumetric elements or triangular prisms 128 fills the space between modeled end diastolic endocardium surface 90 and modeled end systolic endocardium surface 92. The average area of triangular filed sections 124 and 126 comprising the ends of each triangular prism 128 are determined. The volume of triangular prism 128 is determined, and a range of motion of the cardiac wall at that triangular prism is then determined by dividing its volume by the average of the areas of tiled sections 124 and 126 for that triangular prism. This determination is preferably repeated tar each of the triangular prisms filling the space between the inner and outer surfaces of the model.

The second technique for referencing the center surface to anatomic landmarks in the heart is applicable to the third method for determining the center surface. The connected triangles of the mesh representing the inner surface S1 are numbered in reference to the anatomic landmarks. This numbering is transferred to the corresponding connected triangles comprising the mesh representing the center surface when the center surface is initially defined. In the following discussion, the connected triangles comprising the mesh representing a surface can generally be considered equivalent to the tiles of that surface that are referenced in the first two methods for defining the center surface.

Figure 12:
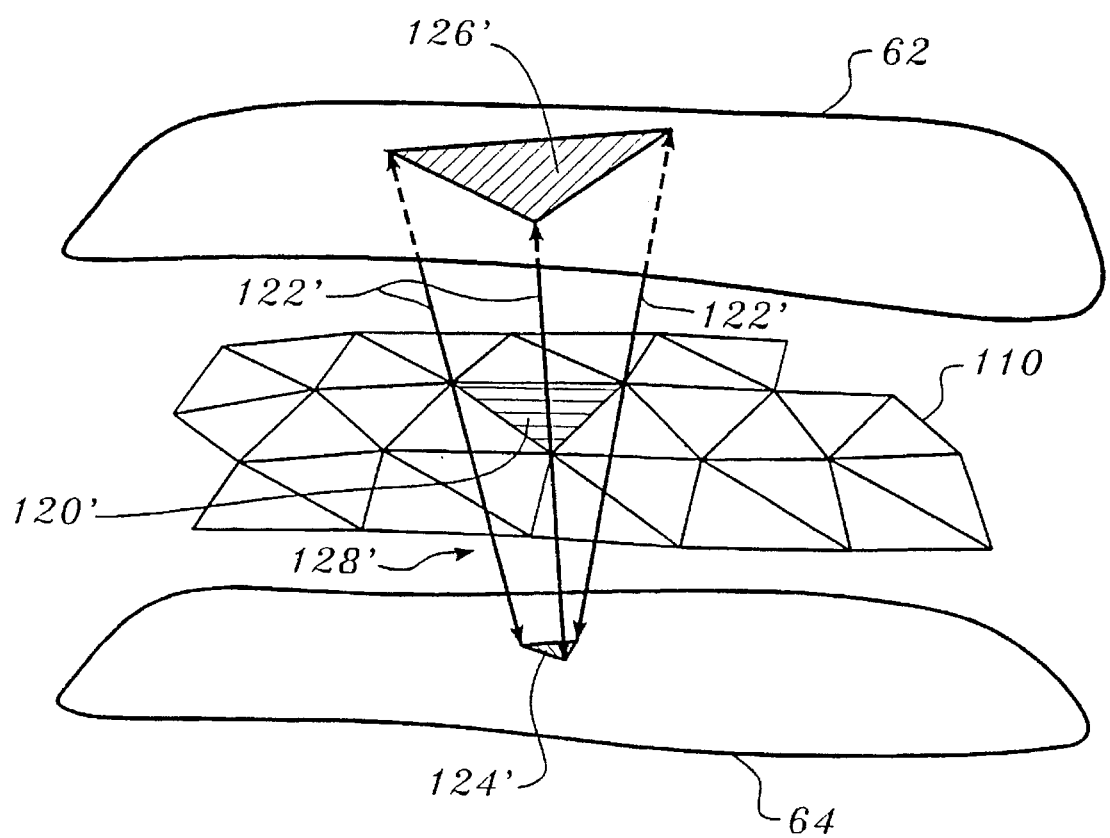
FIG. 12 illustrates how the tiled sections mapped onto the center surface are projected onto the inner and outer surfaces representing the endocardium and epicardium, respectively, to define one of a plurality of triangular prisms used to determine wall thickening.

FIG. 12 displays triangular tiled sections 120' produced by mapping the average center surface template onto the patient's center surface, or by projecting normals from the mesh of connected triangles representing the inner surface, which are numbered, to the corresponding connected triangles comprising the mesh representing the center surface. In either case, triangular tiled section 120' is projected onto both modeled endocardial surface 64 and epicardial surface 62 at end systole, using the technique illustrated in FIG. 11, producing corresponding triangular tiled sections 124' and 126', respectively. The volume of a corresponding triangular prism 128', and the average of the areas of triangular-shaped projected tiled sections 124' and 126' comprising the ends of triangular prism 128' are determined for each such triangular prism filling the space between the inner and outer surfaces of the model. Cardiac wall thickness at end systole is then found by dividing this volume by the area of triangular tiled section 120' for each of the triangular tiled sections comprising the center surface. This procedure is repeated for the model of the endocardial and epicardial surfaces at end diastole to determine thickness of the cardiac wall at each triangular prism at that portion of the cardiac cycle. Thickening of the cardiac wall at a given triangular prism is then simply equal to the difference between the thicknesses at end systole and at end diastole.

Figure 13:
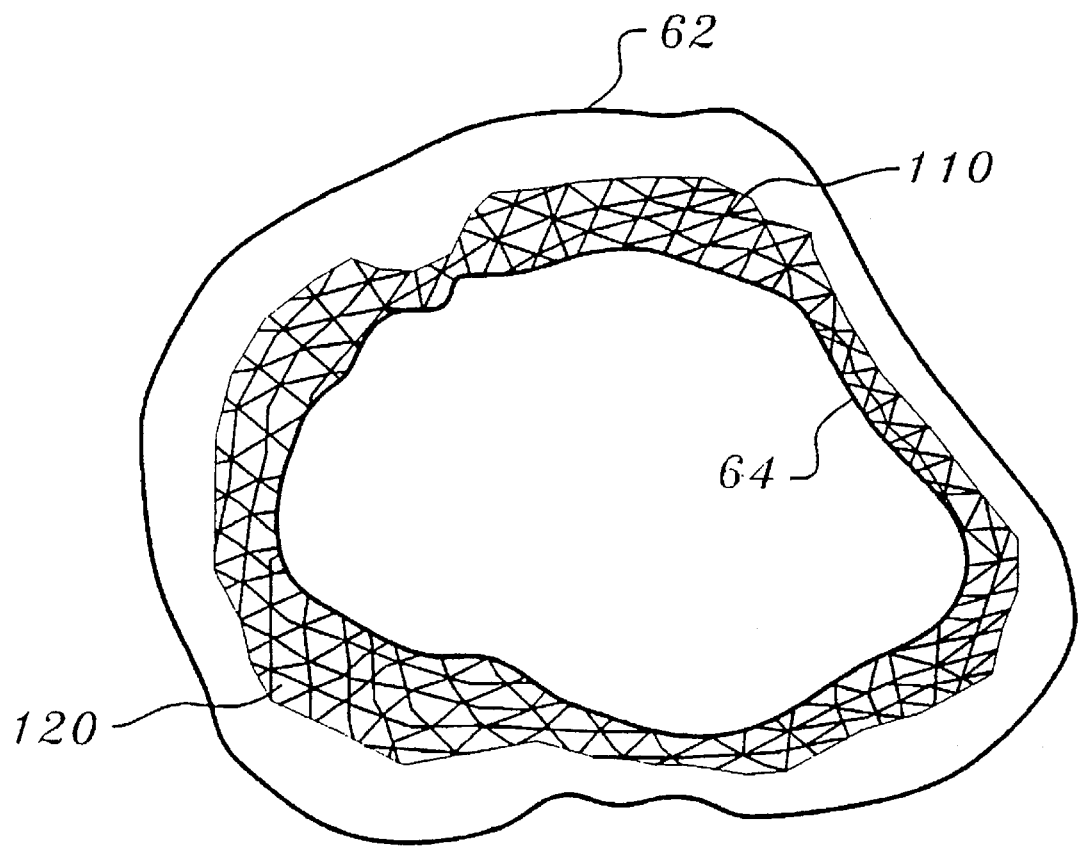
FIG. 13 is a graphic image illustrating a cross section of the modeled inner and outer surfaces and the center surface defined by a plurality of triangles.

In FIG. 13, center surface 110 is illustrated in a cross-sectional view of the left ventricle model, disposed midway between endocardial surface 64 and epicardial surface 62. In reality, this image in presented to the user in color so that cardiac parameters are readily evident based on a defined color coding. For example, the color coding can represent regional cardiac function, or abnormality regional functions, perhaps as expressed in units of standard deviations from the mean of a normal reference population. In this context, regional function is intended to mean one of the following: (a) cardiac wall motion normalized by heart chamber size (corresponding to percent fractional shortening, or wall motion divided by the cube root of the chamber volume at end diastole—in percent); (b) change in wall thickness normalized by heart chamber size (corresponding to wall thickening, which equals wall thickness at end systole minus wall thickness at end diastole); and (c) change in wall thickness normalized by wall thickness at end diastole (corresponding to wall thickening divided by wall thickness at end diastole—expressed in percent). Two different procedures for determining wall thickening are disclosed below, Method A being preferred for regional function (b), and Method B for regional function (c).

By dynamically viewing different cross sections of the left ventricle from different points of view, a medical practitioner can monitor dynamic changes in cardiac function with respect to wall thickness and range of motion of the cardiac wall. To accomplish this procedure in real time, for example during surgery, the step of manually tracing the images of the heart produced by scanning with imaging device 42 must be done automatically by CPU 32, as noted above. Software for automatically tracing along surfaces in an image such as that produced by imaging device 42 to automatically produce the traced border of each image plane is being developed.

Figure 14:
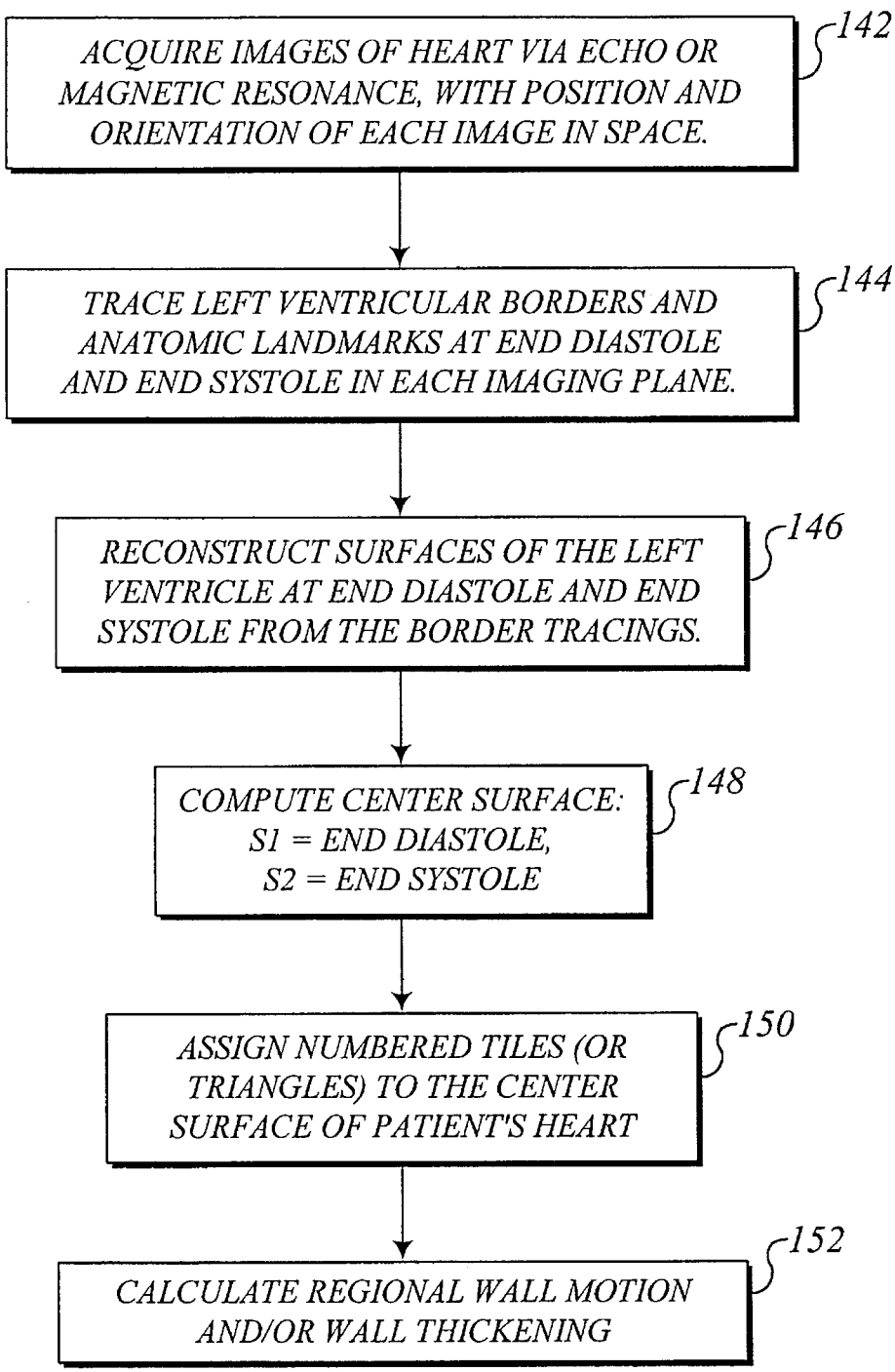
FIG. 14 is a top-level flow chart that generally defines the steps of the method for determining regional wall motion and wall thickening in the heart.

Discussion of Flow Charts and Methodology Used for Determining Cardiac Parameters In FIG. 14, a top-level flow chart indicating each of the steps required to determine regional wall motion and wall thickening are illustrated in a flow chart 140. Starting at a block 142, cardiac imaging and model processing system 30 acquires images of heart 44 using ultrasound echo or magnetic resonance imaging, along with data that define the spatial orientation and position of each image. As noted above, a specific portion of heart 44 that is of interest is scanned, such as the left ventricle. In a block 144, the images acquired by scanning the heart are traced, for example, in the case of the left ventricle, the ventricular borders and anatomic landmarks at end diastole and end systole in each imaging plane. A block 146 provides for reconstructing or modeling the surfaces of the left ventricle or other portion of the heart that was scanned, at both the end diastole and end systole, using the border tracing data, which comprise a series of x, y, and z data points. Next, in a block 148, a center surface is determined, for example, the center surface between the endocardial surface at end diastole and end systole for one model, or the center surface between the epicardial surface and endocardial surface at the end diastole for the other model. One of the three methods discussed above can be used to determine the center surface. In a block 150, the tiles on the center surface are numbered by one of two procedures. In the first procedure, an average tiled section template is matched to the center surface by referencing to the landmarks or anatomical structures in the heart, such as valves and papillary muscles. In the second procedure, the numbering of triangles on the inner surface is transferred to corresponding triangles on the mesh representing the center surface when the initial or trial center surface is created. Finally, in a block 152, using projected tiled sections to generate prism volumetric elements, the regional wall motion and/or wall thickness and thickening are determined.

In acquiring the image data using transesophageal ultrasonic probe 50, the patient is anesthetized, using a combination of high-dose narcotics such as ALFENTANIL™ and a benzodiazapine, such as MIDAZOLAM™. These agents do not depress myocardial contractility to any significant degree and are of relatively short duration. During surgery, an appropriate intracardial monitoring technique should be selected by the anesthesiologist as appropriate for the particular patient and operative procedure, but will at least involve continuous ECG monitoring and non-invasive recording of blood pressure.

The imaging is performed after providing compensation for vasodilation due to the Alfentanil, by fluid administration and after hemodynamic stability has been achieved. The transesophageal ultrasonic probe is initially inserted, and preferably, a complete two-dimensional and color Doppler examination is made and recorded, that includes both ventricles, both atria, and the valves in heart 44. This preliminary two-dimensional examination will be useful to guide fluid administration and to achieve a truly uevolemic state prior to the three-dimensional imaging and modeling.

The imaging required for three-dimensional modeling is made during suspended ventilation, between periods of cauterization. Due to the flexibility of the transesophageal ultrasonic probe, images can be recorded for both the transverse (short) and longitudinal (long) axes from multiple positions within esophagus 48 (FIG. 2) or from within the stomach, as necessary to obtain a complete visualization of the left ventricle or other portion of the heart being imaged. During this imaging process, it is contemplated that up to forty image planes will be recorded and identified, based upon the specific positions of the transesophageal ultrasonic probe.

Figure 15:
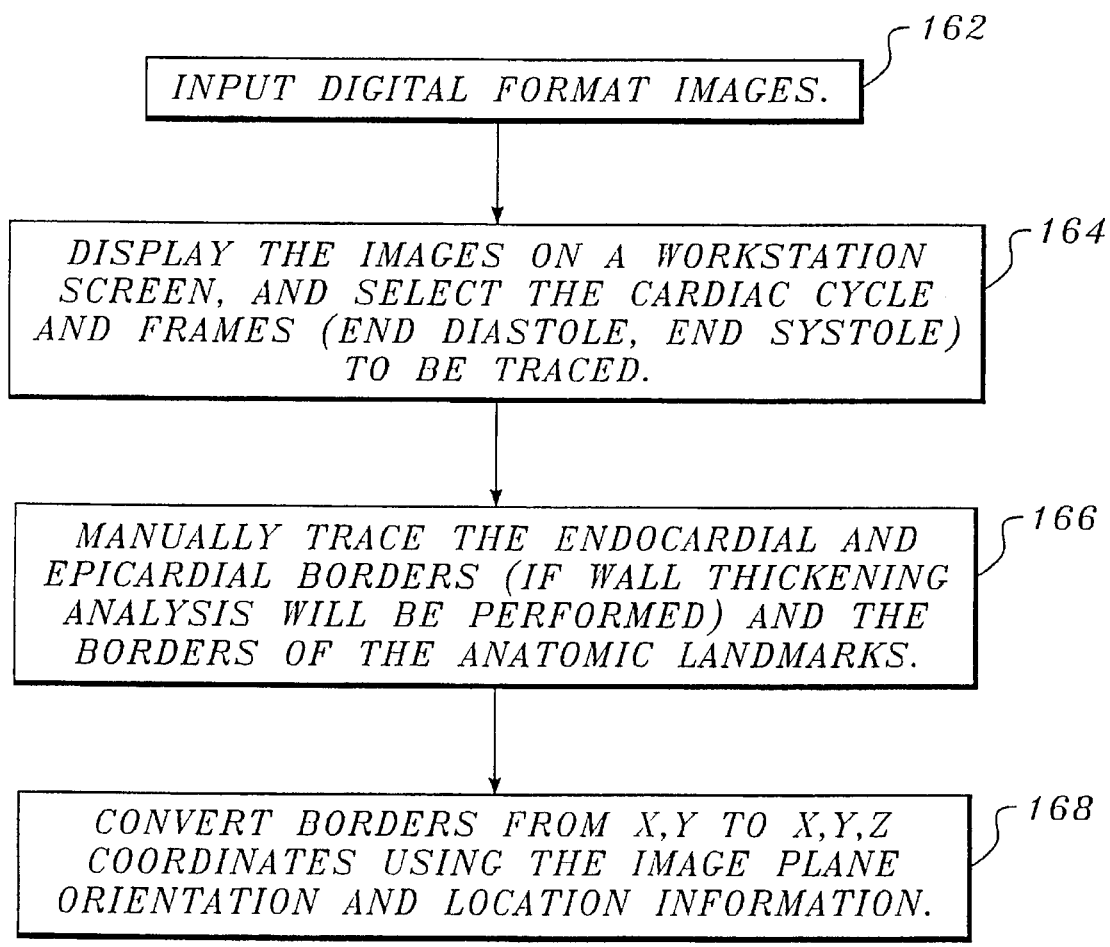
FIG. 15 is a flow chart illustrating the logical steps employed in tracing a border of a displayed image of a portion of the heart.

Using either the ADC provided in ADC and image processor 40 (or alternatively, using a frame grabber), the image data developed by transesophageal probe 50 are converted to digital format and displayed on graphics display 34, as described above. These two steps are covered in blocks 162 and 164 in FIG. 15. Further, as noted in blocks 164 and 166, the particular image plane and the ECG are displayed during the tracing. The endocardial and epicardial surfaces of the image planes selected in a block 164 are thus traced, along with any anatomic reference landmarks in the particular views of the heart being imaged.

Figure 16:
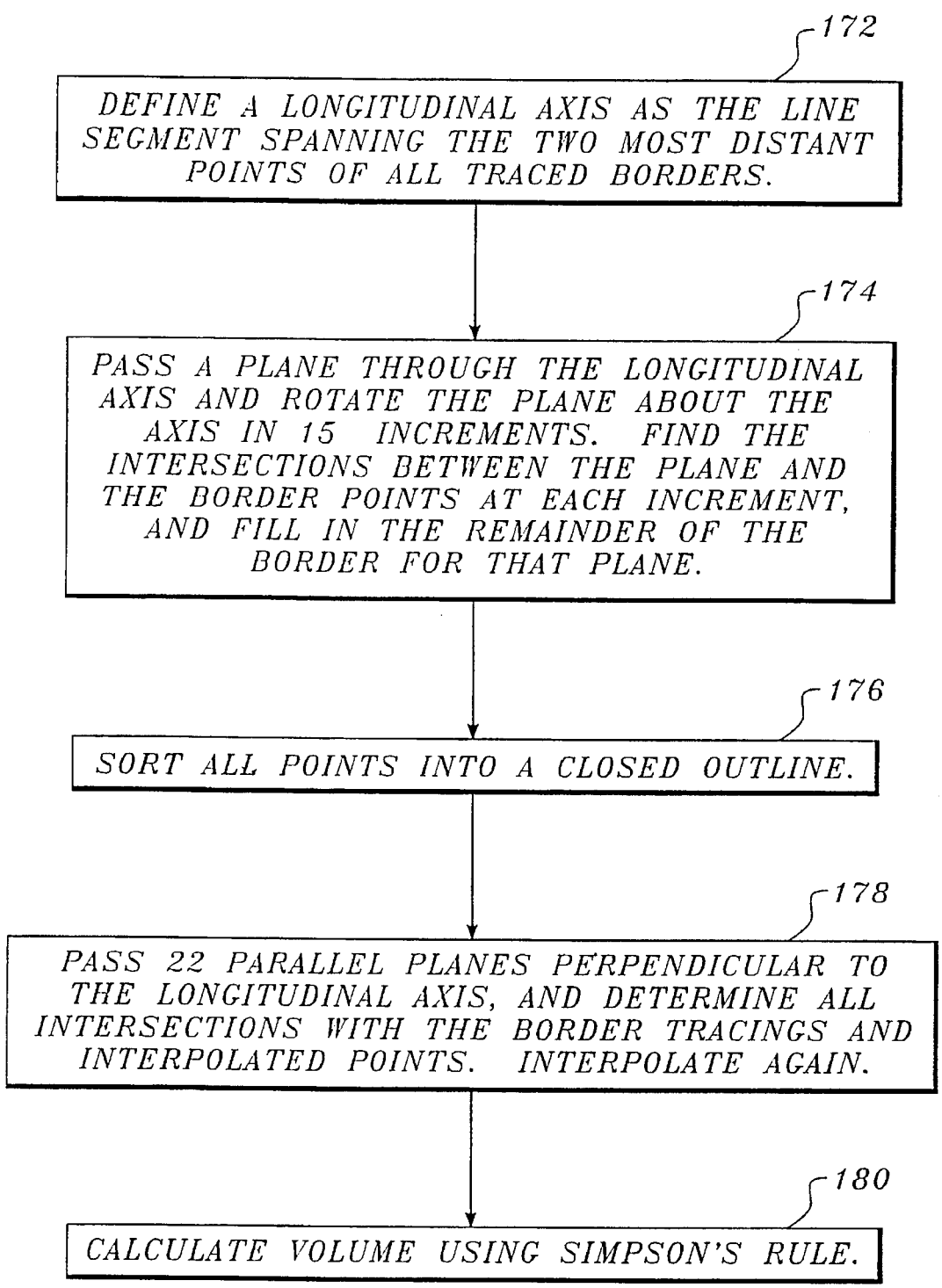
FIG. 16 is a flow chart that identifies the steps used to generate a three-dimensional model of the portion of the heart imaged and the determination of volume and ejection fraction.

Preferably, modeling of the data produced by tracing each of the image planes as described above is reconstructed to provide a three-dimensional model of an inner and outer surface using the technique represented by the steps of flow chart 170 in FIG. 16. In a block 172, a longitudinal (long) axis for the left ventricle is defined as a line segment spanning the two most distant points of all of the traced borders. A plane is then passed through this longitudinal (long) axis and rotated about the axis in increments of 15° in a block 174. At each incremental rotation, the intersection points between the plane and the original border points determined by tracing is found and the remainder of that border for the plane is filled in using a spline curve filling technique, except at the mitral and aortic valve planes. At the intersections of this rotating plane with the valve planes, the border points are connected by straight line segments, so that the model being produced has a ruled surface in these two valve regions.

The original points developed by tracing and those subsequently developed by fitting the points on the successfully rotated planes are then sorted into a closed outline in a block 176. The set of longitudinal interpolated borders comprising this outline resembles the slices of an orange. In order to find the volume of the left ventricle, a series of 22 planes is passed perpendicularly to the longitudinal (long) axis of the above-generated model in a block 178. The intersection points between these transverse axis planes and the longitudinal interpolated borders is determined and sorted to provide a closed outline. In a block 180, the resulting parallel cross-sectional interpolated borders is summed according to Simpson's rule to determine volume.

A number of commercially available software programs are able to convert the Cartesian data points developed in block 180 to a three-dimensional model surface. Examples of such software include: SILVER SCREEN™ (produced by Schroff Development Corporation), and AVS™ (produced by Advanced Visual Systems Inc.). To provide three-dimensional modeled surfaces that can be properly rendered and shaded, the data are best entered as surface tiles comprising three points in space that define a triangle. By connecting these surface tiled triangles, a three-dimensional surface is generated that can be properly rendered for graphic visualization. When producing the three-dimensional model, the coordinates of the position of the probe when it acquired each of the imaging planes, the position of the first, middle, and last scanned image plane, the position of a plane passing through a midline of all of the scanning sectors, a centroid of the most basal and apical imaging planes, and anatomical markings are used.

Figure 17:
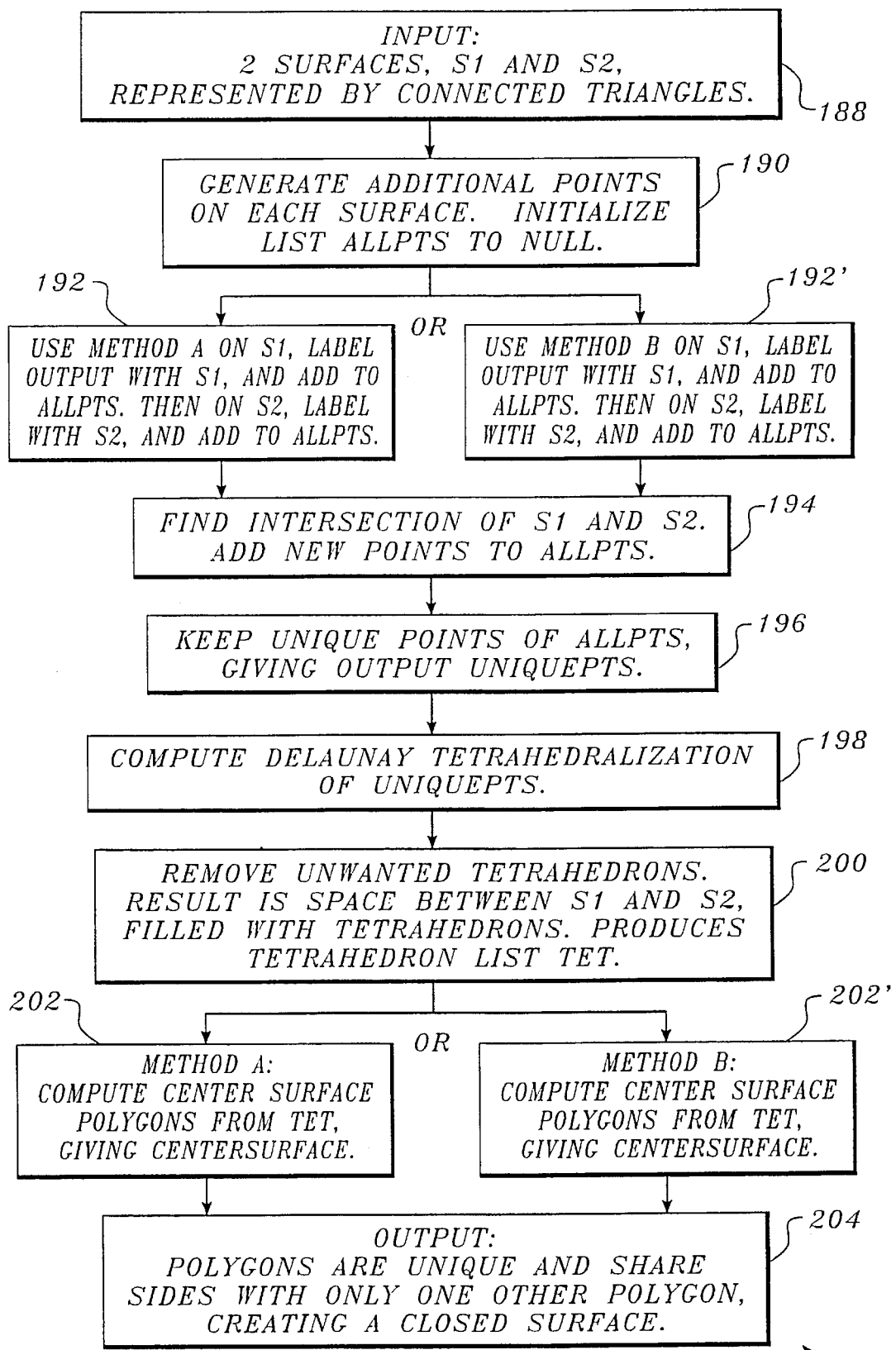
FIG. 17 is a flow chart illustrating the logical steps employed for a first method for generating the center surface.

Once the modeled surfaces have been rendered, a center surface located medially between the modeled inner and outer surfaces is generated in accordance with the method outlined in the steps of a flow chart 186 shown in FIG. 17. Starting at a block 188, two surfaces, S1 and S2, in respect to which the center surface is to be generated and represented by connected triangles, are input. In a block 190, additional points on each surface are generated by interpolation to improve the resolution with which the center surface is developed, and a variable AllPts is initialized to a null value.

There are two alternative approaches used to generate the additional interpolated points on a surface, identified as Method A, in a block 192, and as Method B, in a block 192'. One of these two methods is selected to produce the additional interpolated points, adding each of these points to the respective surfaces S1 and S2.

Figure 18:
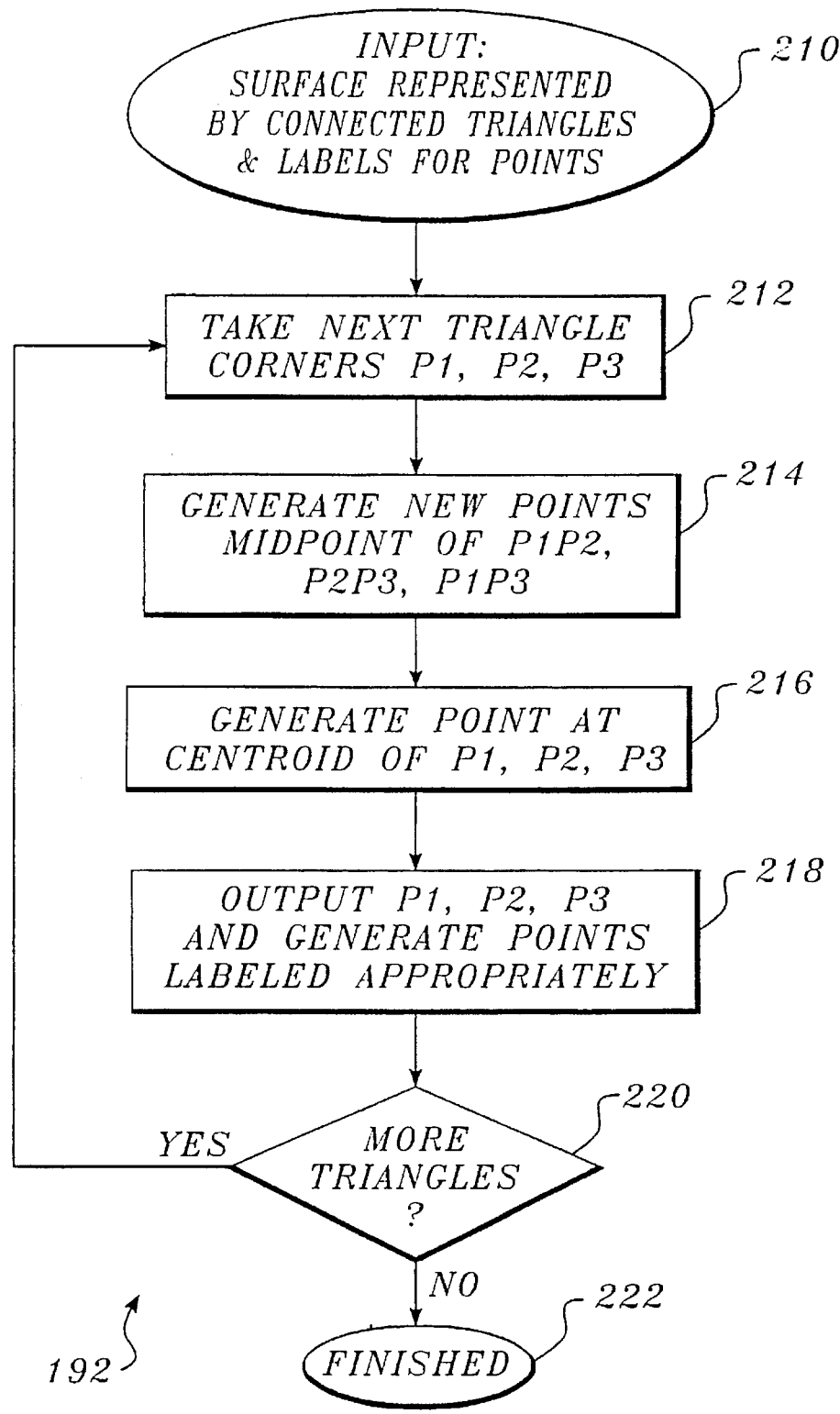
FIG. 18 is a flow chart that shows the steps followed in one embodiment, to generate additional points on a model surface, to improve resolution.

Turning to FIG. 18, details of Method A are disclosed in flow chart 192 starting at an input block 210, wherein one of the surfaces S1 or S2 is input. (Note that in this and other instances that follow, a reference number assigned to a block in FIG. 17 is used in connection with a corresponding flow chart that provides the details of that block.) In a block 212, successive triangles on the surface defined by corner points P1, P2, and P3 are taken up. New points are generated at the midpoints of the line segments P1P2, P2P3, and P1P3 in a block 214. In addition, a point at a centroid of the triangle defined by points P1, P2, and P3 is generated in a block 216. Each of the points comprising the corners of the triangle and the generated interpolated points, labeled appropriately, are output in a block 218. A decision block 220 then determines if more triangles on the selected surface are available to be processed, and if so, returns to block 212. Otherwise, the procedure is finished, as indicated in a block 222.

Figure 19:
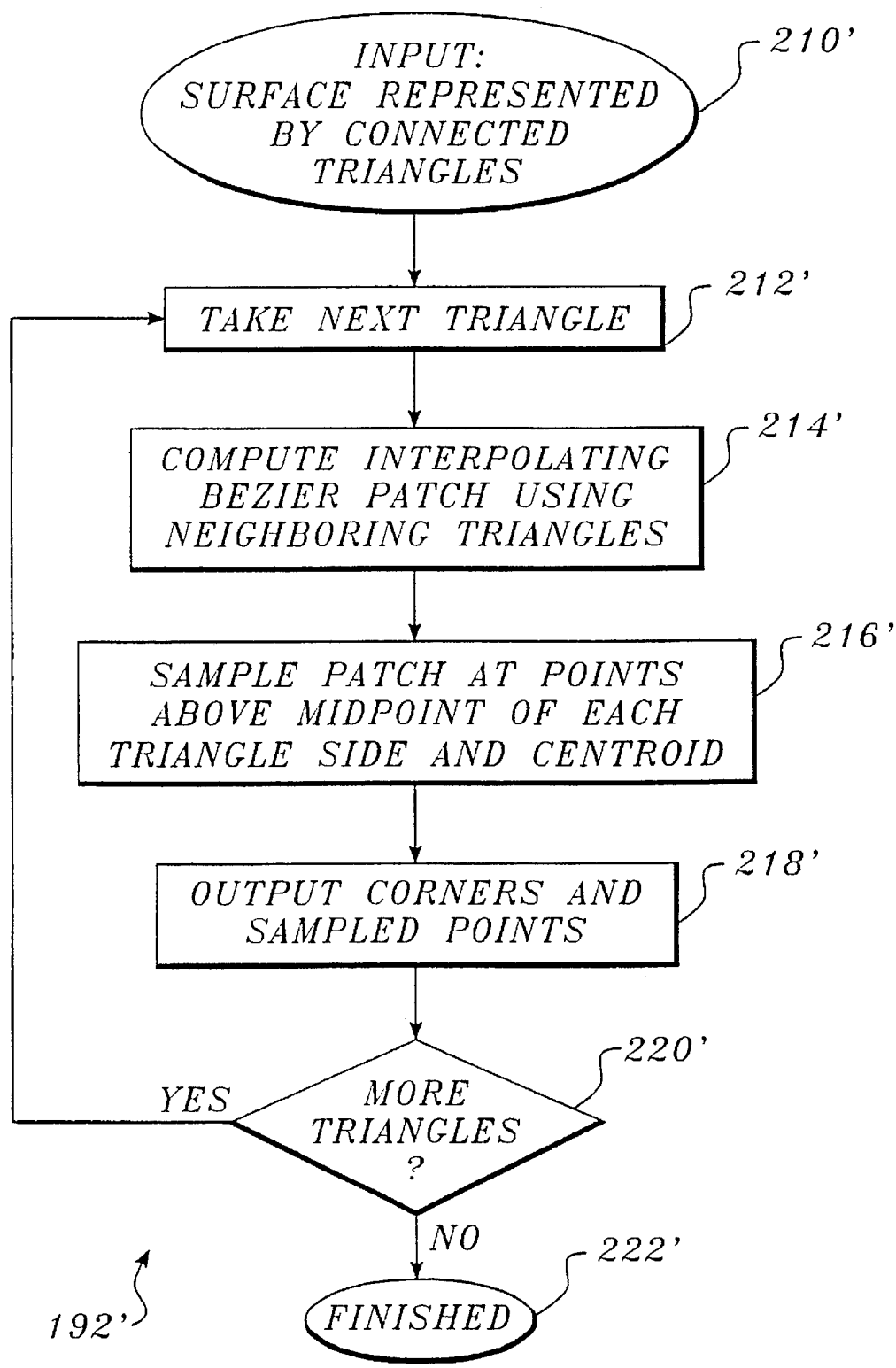
FIG. 19 is a flow chart that shows the steps followed in another embodiment, to generate additional points on a model surface to improve resolution.

In Method B, identified by flow chart 192' in FIG. 19, the surface to be processed is input at a block 210'. Successive triangles are processed, as indicated in a block 212', leading to a block 214' wherein an interpolated Bezier patch (not shown) is determined using each of the neighboring triangles around a triangle being processed. Thereafter, in a block 216', the Bezier patch is sampled at the points above the midpoint of each side of the triangle and at its centroid. In a block 218', the corner points and the sampled points (the interpolated points) are output. A decision block 220' then determines if additional triangles remain to be processed, and if so, returns to block 212'. Otherwise, the process is completed, as indicated in a block 222'.

Figure 20:
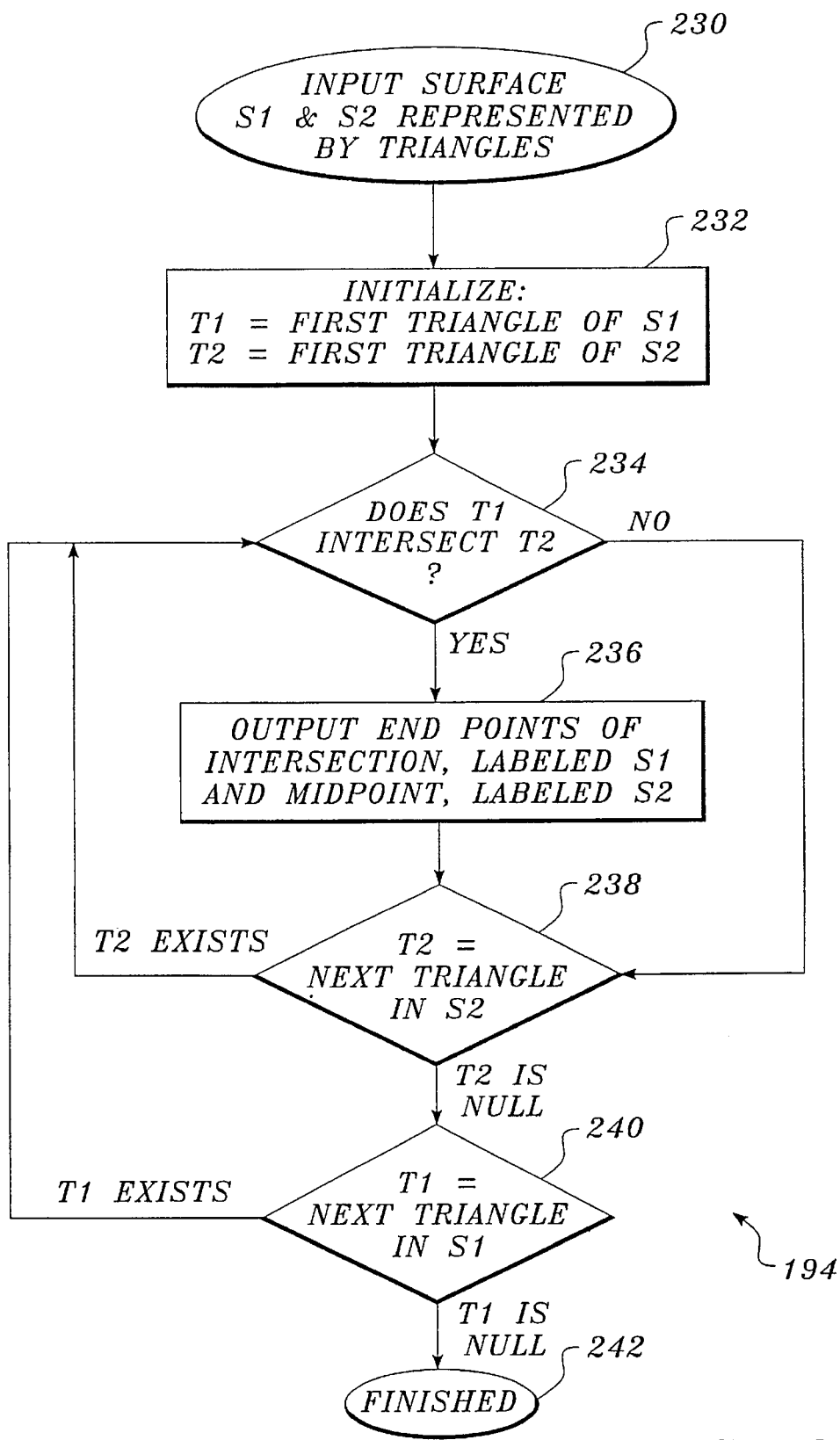
FIG. 20 is a flow chart illustrating the steps used to find the intersection of two surfaces.

Turning back to FIG. 17, a block 194 provides for finding the intersection of surfaces S1 and S2 and adding points along the intersection to the data AllPts. Details of this process are disclosed at flow chart 194 in FIG. 20. Starting at a block 230, surfaces S1 and S2, represented by the connected series of triangles, are input. In a block 232, variables T1 and T2 are respectively initialized to the first triangles of surfaces S1 and S2, respectively. A decision block 234 then determines whether triangle T1 intersects triangle T2, and if so, proceeds to a block 236, in which the procedure produces as output end points of the intersection, labeled S1 and the midpoint, labeled S2. Thereafter, T2 is set to the next triangle in S2 (if it exists) in a decision block 238. Assuming that another triangle on surface S2 remains to be processed, the logic returns to decision block 234 and otherwise, proceeds to a decision block 240. In decision block 240, the logic determines if another triangle T1 on surface S1 remains to be processed, and if so, proceeds back to decision block 234. If not, the program finishes at a block 242.

Figure 21:
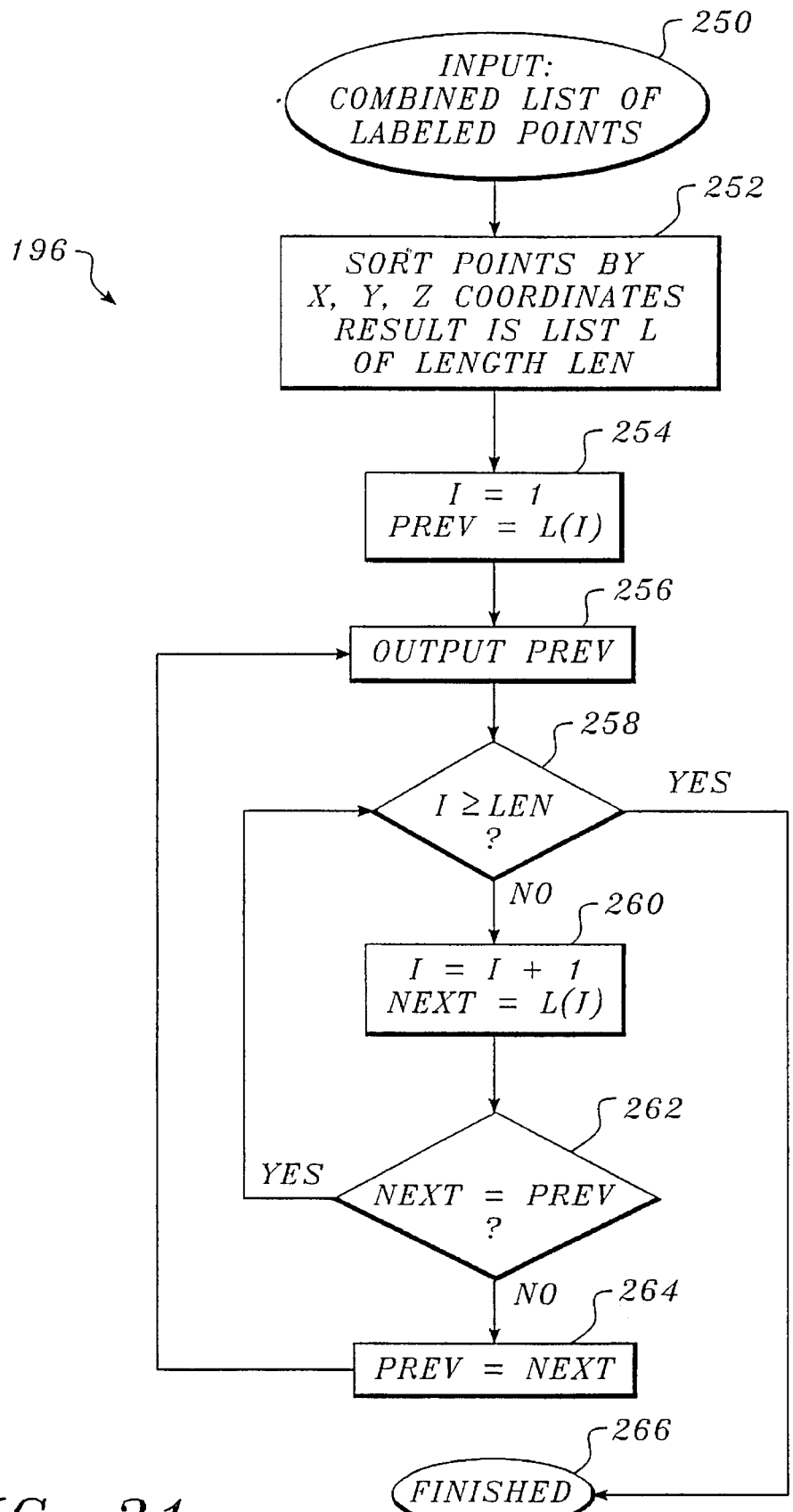
FIG. 21 is a flow chart the defines the steps followed to identify the points on a surface that will be retained.

Again returning to FIG. 17, a block 196 indicates that the next step is to keep unique points in the data AllPts, providing output data called "UniquePts." Details of this procedure are shown in FIG. 21 at flow chart 196. Beginning at an input block 250, a combined list of labeled points on surfaces S1 and S2 are input. In a block 252, the points defined by the Cartesian coordinates x, y, and z are sorted producing a list L of length LEN. In a block 254, I is initialized to one and the variable PREV is initialized to L(I). In a block 256, the value of the variable PREV is output, followed by a decision block 258, which determines if the value of I is greater than or equal to the variable LEN. If not, a block 260 increments the value of I by one and sets a variable NEXT equal to L(I). Then, a decision block 262 determines if NEXT equals PREV. If so, the logic returns to decision block 258. Otherwise, it proceeds to a block 264 which sets PREV equal to NEXT. The logic then returns to block 256 and finishes whenever the inquiry of decision block 258 is affirmative, indicating that the value of I is equal to or greater than LEN. An affirmative response to decision block 258 leads to a block 266, in which the process for comparing the coordinates for consecutive points in decision block 262 is used to process each of the data points to finish this portion of the process. If it is determined that any two points have the same coordinates, then one of these duplicate points is deleted. After all such points have been processed, only unique points remain in the database, with no duplicates.

Figure 22:
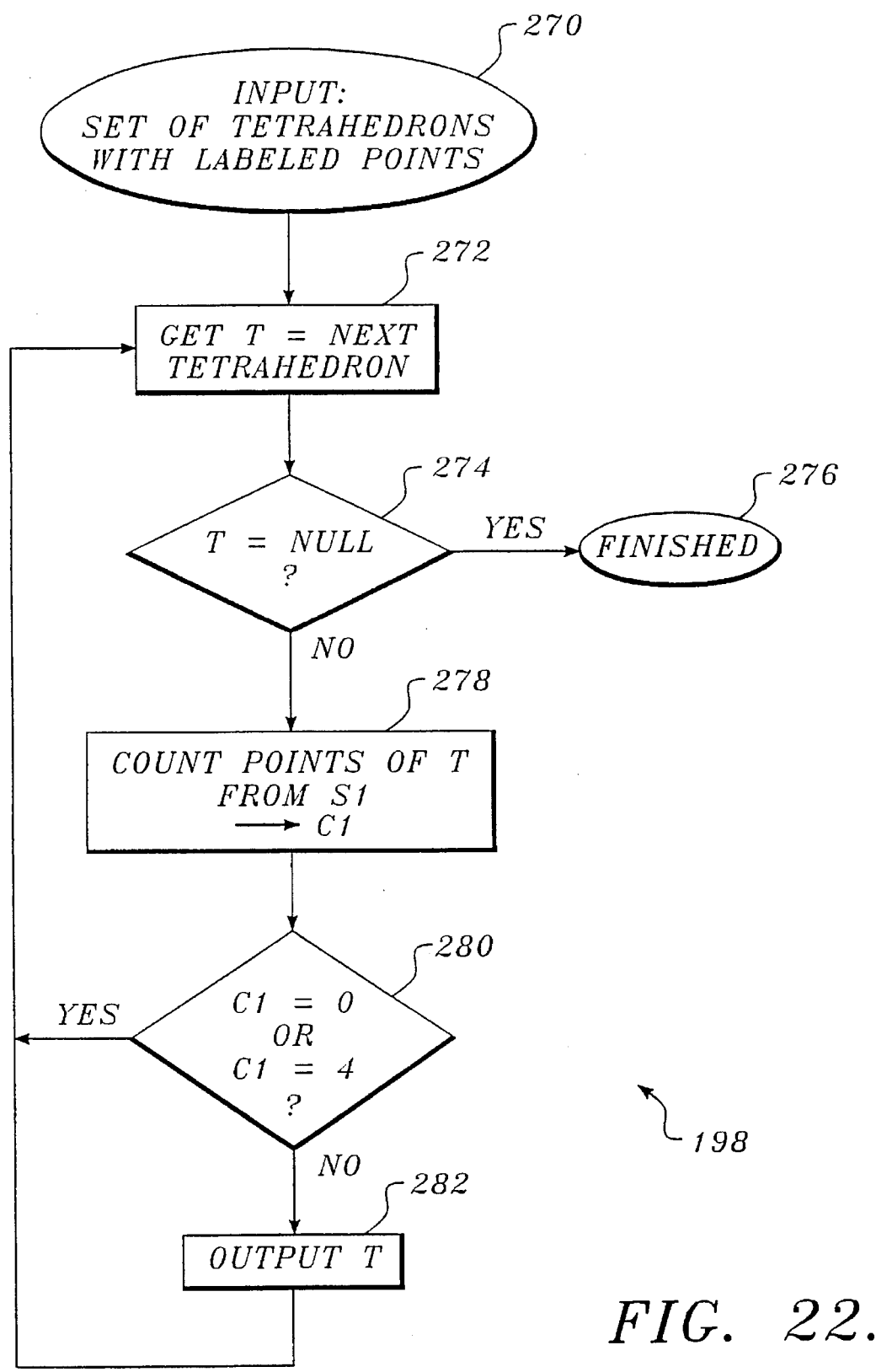
FIG. 22 is a flow chart that shows a first procedure for retaining the tetrahedrons spanning the space between the two surfaces.

Again returning to FIG. 17, the next step provides for computing Delaunay tetrahedralization of the unique points, in a block 198. Details of this process are disclosed in flow chart 198, shown in FIG. 22. There are several well-known techniques in the prior art for computing Delaunay tetrahedralization. The result of this computation is a set of tetrahedrons whose sides connect points from an input set, with the properties that a sphere circumscribing the tetrahedron does not contain any other points in the set, and that the center of the sphere lies close to the medial axis of the tetrahedron. Referring to FIG. 22, the procedure for determining the tetrahedrons that span a distance between two adjacent surfaces is disclosed starting at an input block 270, which provides for input of a set of tetrahedrons with labeled points that define the vertices of the tetrahedrons. In a block 272, a parameter T is set equal to the next tetrahedron in the plurality of tetrahedrons spanning the distance between the two surfaces. A decision block 274 then determines if all tetrahedrons have been processed and if so, proceeds to a block 276, indicating that the procedure is finished. Otherwise, the logic proceeds to a block 278, wherein the number of points comprising the tetrahedron on surface S1 is assigned to a variable parameter C1. In a decision block 280, the logic determines if the variable C1 is equal to either 0 or 4, and if so, returns to block 272 to process the next tetrahedron. Otherwise, the tetrahedron assigned to the variable T is output in a block 282; the logic then returns to block 272.

Figure 23:
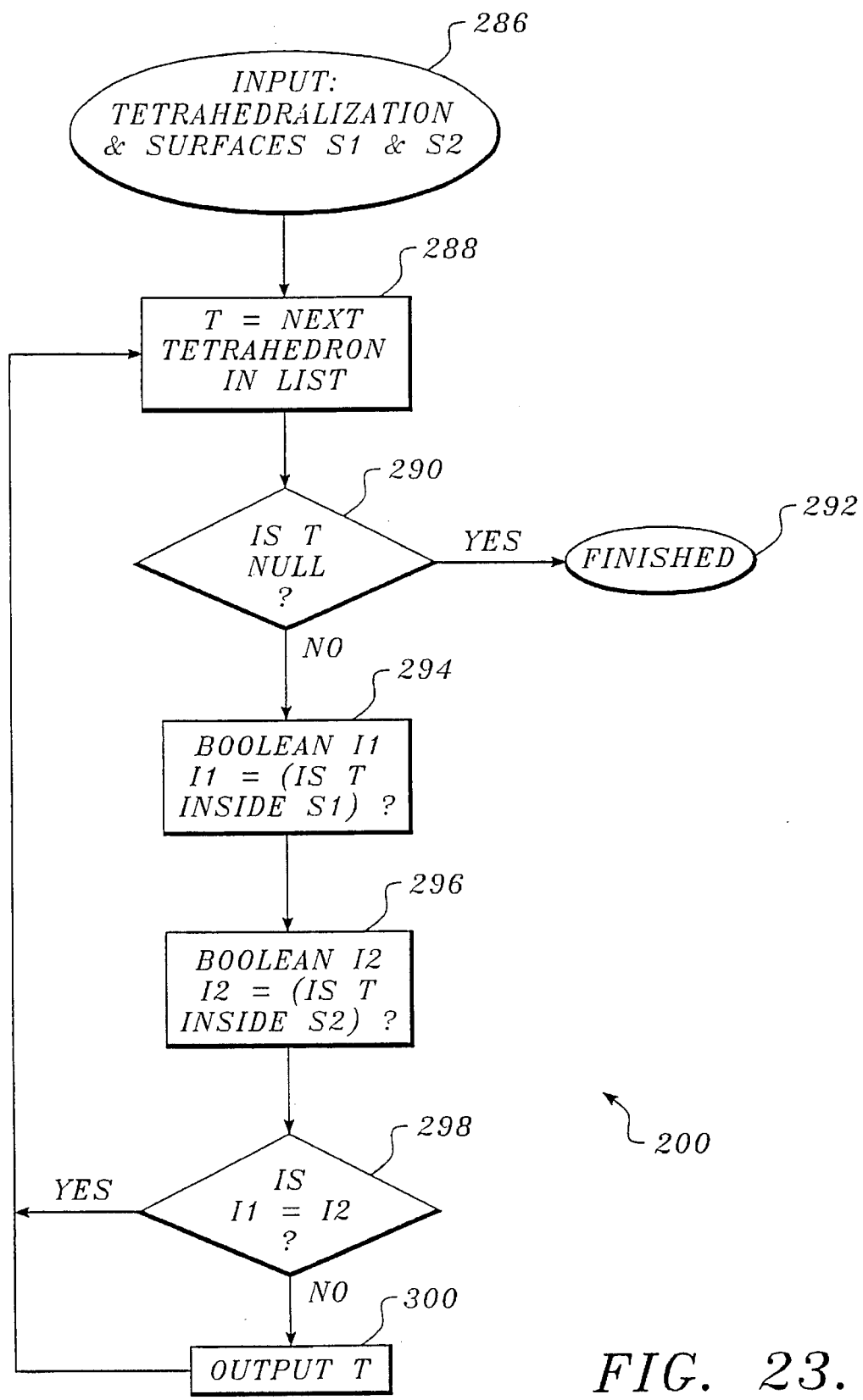
FIG. 23 is a flow chart of the procedure for removing unwanted tetrahedrons produced by the procedure of FIG. 22.

Looking back on FIG. 17, a block 200 identifies the next step as removing unwanted tetrahedrons to produce a space between surfaces S1 and S2 that is filled with tetrahedrons. This procedure produces a tetrahedron list labeled TET. Details of the procedure are shown within FIG. 23 in a flow chart 200. Starting at a block 286, the tetrahedralization data previously developed and surfaces S1 and S2 are input. Again, in a block 288, the variable T is set equal to the next tetrahedron in the list of tetrahedrons returned by the previous procedure. Thereafter, a decision block 290 determines if all of the tetrahedrons have been processed, and if so, sets the variable T equal to NULL. If no other tetrahedrons remain to be processed, the procedure concludes, in a block 292. Otherwise, it proceeds to a block 294. In block 294, a Boolean expression I1 is defined as TRUE if the tetrahedron last assigned to the variable T is inside the surface S1, and FALSE, if not. Subsequently, in a block 296, a Boolean variable I2 is defined as TRUE if the tetrahedron T is inside the surface S2, and FALSE if not. A decision block 298 then determines whether the tetrahedron T is inside both surfaces or outside both surfaces, by determining if the Boolean expressions I1 and I2 are equal. If so, the next tetrahedron is processed by returning to block 298, thereby filtering the previous tetrahedron from the output. Otherwise, the tetrahedron equal to T is output in a block 300 before returning to block 298.

Figure 24:
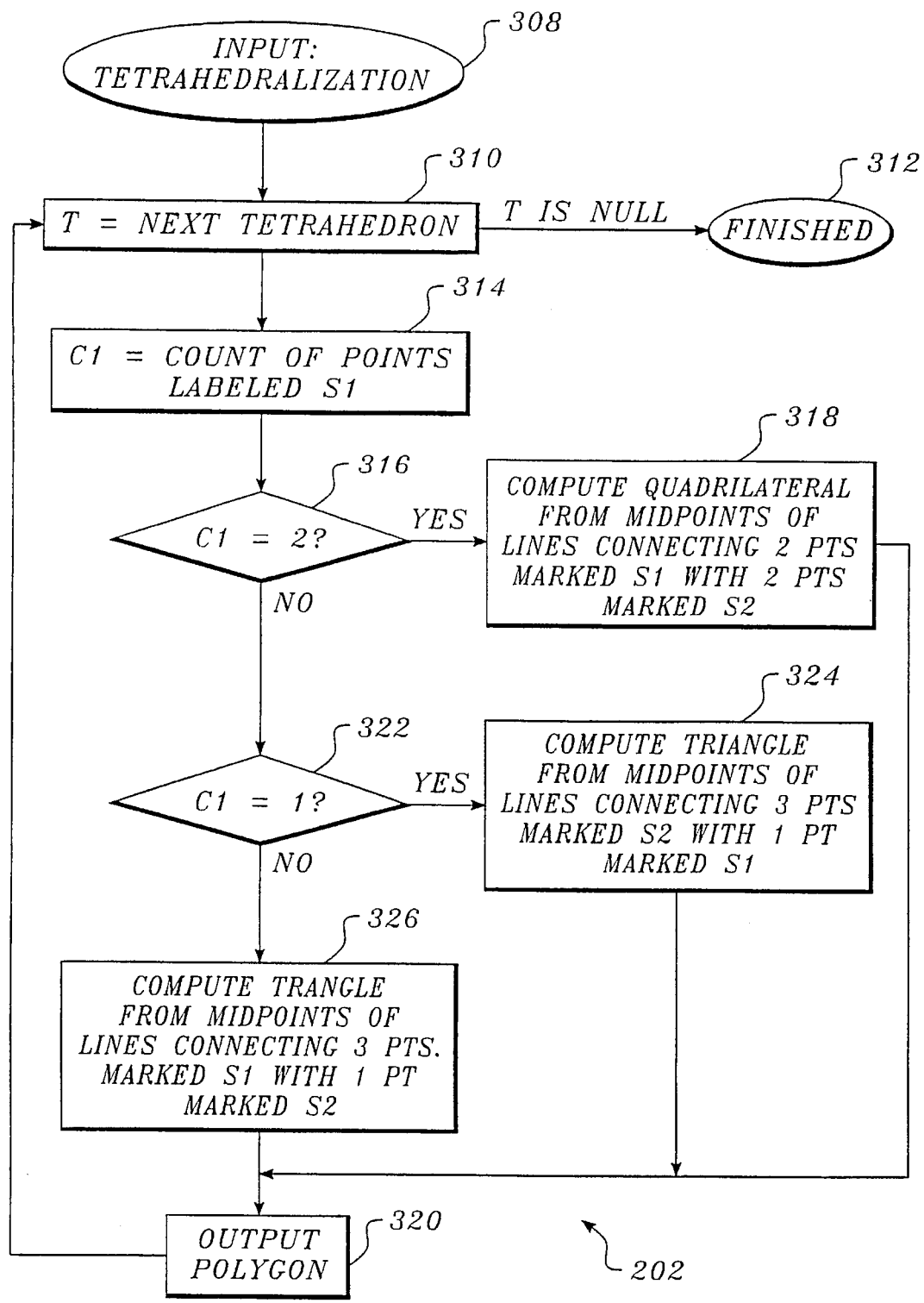
FIG. 24 is a flow chart illustrating the steps of a first procedure for determining center surface polygons.

Looking back at FIG. 17, there are two alternative steps for computing the center surface polygons, and these methods are identified by a block 202 and a block 202', respectively. Block 202 references a Method A, whereas block 202' references a Method B, both of which produce the center surface from the tetrahedrons. Details of Method A for determining the center surface polygons are shown in FIG. 24 at a flow chart 202, beginning with an input block 308. In the input block, the list of tetrahedrons produced from the previous steps are input, and in a block 310, are sampled one at a time, until no further tetrahedrons remain. In a block 312, the process is concluded. As each tetrahedron in succession is set equal to T; a block 314 provides for counting the number of points in the tetrahedron that are labeled as being on surface S1 and assigning that count to a variable C1. A decision block 316 then determines if C1 equals 2 and if so, a block 318 defines a quadrilateral polygon from midpoints of the lines interconnecting two points marked as being on surface S1 with two points marked as being on the S2 surface. Thereafter the logic proceeds to a block 320, which provides for output of the quadrilateral polygon.

Assuming that the result of the inquiry in decision block 316 is negative, a decision block 322 determines if the variable C1 is equal to 1, and if so, a block 324 computes a triangle from the midpoints of the lines connecting three points that are on the S2 surface with one point that is marked as being on the S1 surface. Thereafter, the logic again proceeds to block 320. A negative response from decision block 322 leads to a block 326, which computes a triangle from the midpoints of the lines connecting the three points that are on the S1 surface with one point that is marked as being on the S2 surface. Again, the logic then proceeds to block 320 to output the polygon and thereafter, returns to block 310 to process the next tetrahedron. Accordingly, it will be apparent that either a quadrilateral or a triangular polygon is determined, depending upon the arrangement of the points on each of the surfaces.

Figure 25:
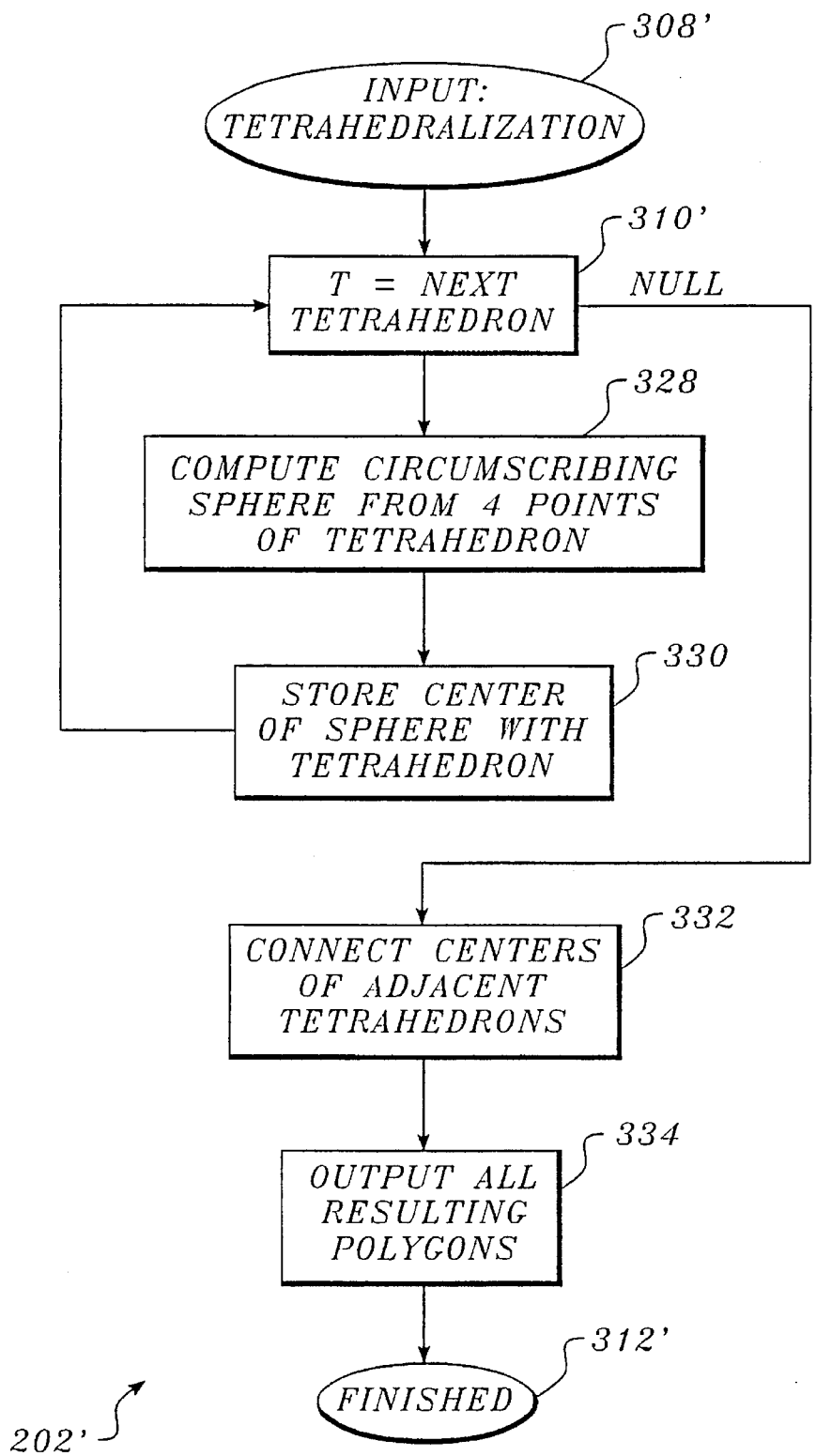
FIG. 25 is a flow chart illustrating the steps of a second alternative procedure for determining center surface polygons.

Proceeding to FIG. 25, a flow chart 202' provides the steps of Method B, starting at a block 308' where again, the tetrahedrons developed from the previous steps are input. A block 310' successively processes the tetrahedrons, setting each one in turn to the variable T until no other tetrahedrons remain any longer, leading to a block 332. After T is set equal to a tetrahedron to be processed, a block 328 provides for computing a circumscribing sphere from the four corner points of the tetrahedron. Thereafter, a block 330 indicates that the center of the sphere is stored for the tetrahedron, before returning to block 310' to process the next tetrahedron. Thus, a succession of spheres developed from the four corner points of the tetrahedron are computed and stored with their center points, until the space between the two surfaces is filled and no further tetrahedrons remain to be processed. The logic then proceeds with block 332, which connects the centers of adjacent tetrahedrons, (i.e., the centers of the spheres). A block 334 then outputs all of the resulting polygons produced by connecting the centers of the spheres, leading to a block 312', wherein the process is finished.

Returning to FIG. 17, a block 204 provides for output of the polygons that are unique and which share sides with only one other polygon, thereby creating a closed surface. This closed surface is the center surface.

Figure 26:
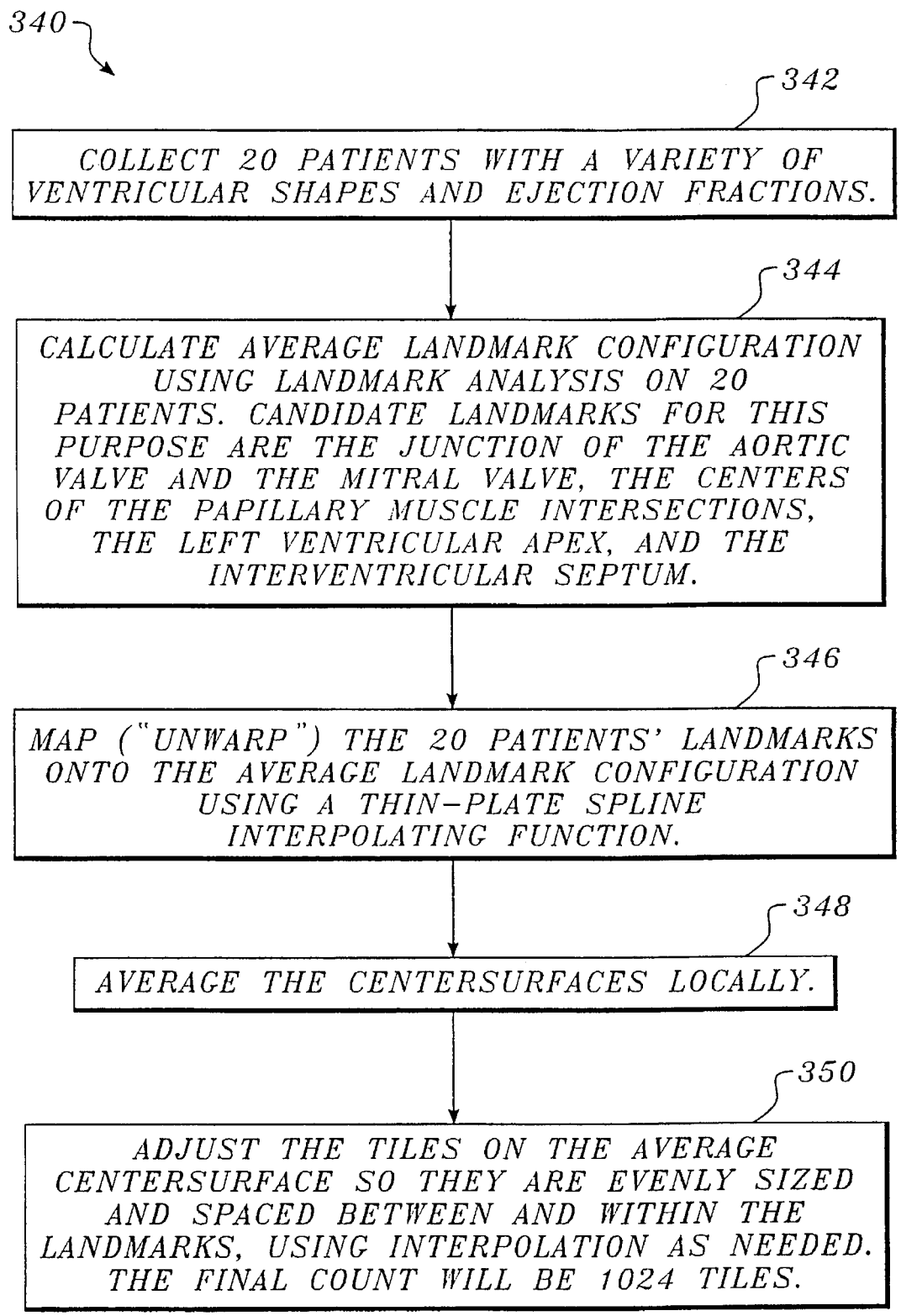
FIG. 26 is a flow chart of the steps used in determining an average center surface for use as a referential template.

The next step in the overall process requires that the average center surface template be applied to map triangular tiled sections from the template onto the center surface for the patient's heart 44. (This step is not implemented if the third method for determining the center surface represented by a mesh of connected triangles is used.) The steps of this process are indicated in a flow chart 340 shown in FIG. 26. In a block 342, a number of patients sufficient to comprise a reasonable statistical sample, for example, twenty, are identified as having a variety of ventricular shapes and ejection fractions. Using landmark reference points within the cardiac structure, a block 344 provides for determining an average landmark configuration for the ventricles of all of the sample subjects. As noted above, the reference landmarks for this purpose includes anatomical attributes such as the junction of the aortic valve and the mitral valve, centers of the papillary muscle insertions, the left ventricular apex, and the interventricular septum.

A block 346 provides for mapping the landmarks for the twenty subjects' cardiac data onto the average landmark configuration using a thin-plate spline interpolating function. Then, in a block 348, the center surfaces for each of these patients are averaged locally, defining averaged triangular filed sections on that center surface. A block 350 then adjusts the tiled sections on the average center surface so that they are evenly spaced and spaced between and within the reference landmarks, applying interpolation as required. Preferably, the final count of triangular tiled sections in the averaged center section template is 1,024.

In order to determine regional wall motion, the steps shown in FIG. 27 for a flow chart 356 are implemented. At a block 358, the average center surface tiled section template is mapped to an individual patient's center surface, derived as explained above, using a thin-plate spline interpolating function. In a block 360, a chord is constructed at each corner of each tiled section, generally normal to the average plane of all tiled sections converging at that corner. As noted above, the normal to an average plane has an orientation determined by adding all of the unit vectors normal to tiled sections converging at the corner of the center section tiled sections through which the chord is to extend. This chord extends to the intersection with the modeled end diastolic and end systolic surfaces. The points of the intersection between the chords and each modeled surface effectively transfers or projects the tiled section from the patient's center surface to the patient's endocardial end diastolic and end systolic modeled surfaces.

In a block 362, the regional wall motion for each of the tiled sections on the end diastolic modeled surface is determined by initially determining the volume of the triangular prism defined by the tiled section projected on the end diastolic modeled surface and the corresponding tiled section projected on the end systolic modeled surface, and by the chords that connect the corners of these two end triangular tiled sections. Next, the average area of the ends of the triangular prism is determined (for each triangular prism). The volume of the prism is divided by the average area of the ends of the triangular prism (this average generally corresponding to the area of the triangular tiled section on the center surface or the area of the triangle comprising the mesh representing the center surface), for each of the triangular prisms. The result of this division is the height or length of the triangular prism, which represents the extent or range of motion of the endocardium surface between the end diastole and end systole at that point on the cardiac wall.

Figure 28:
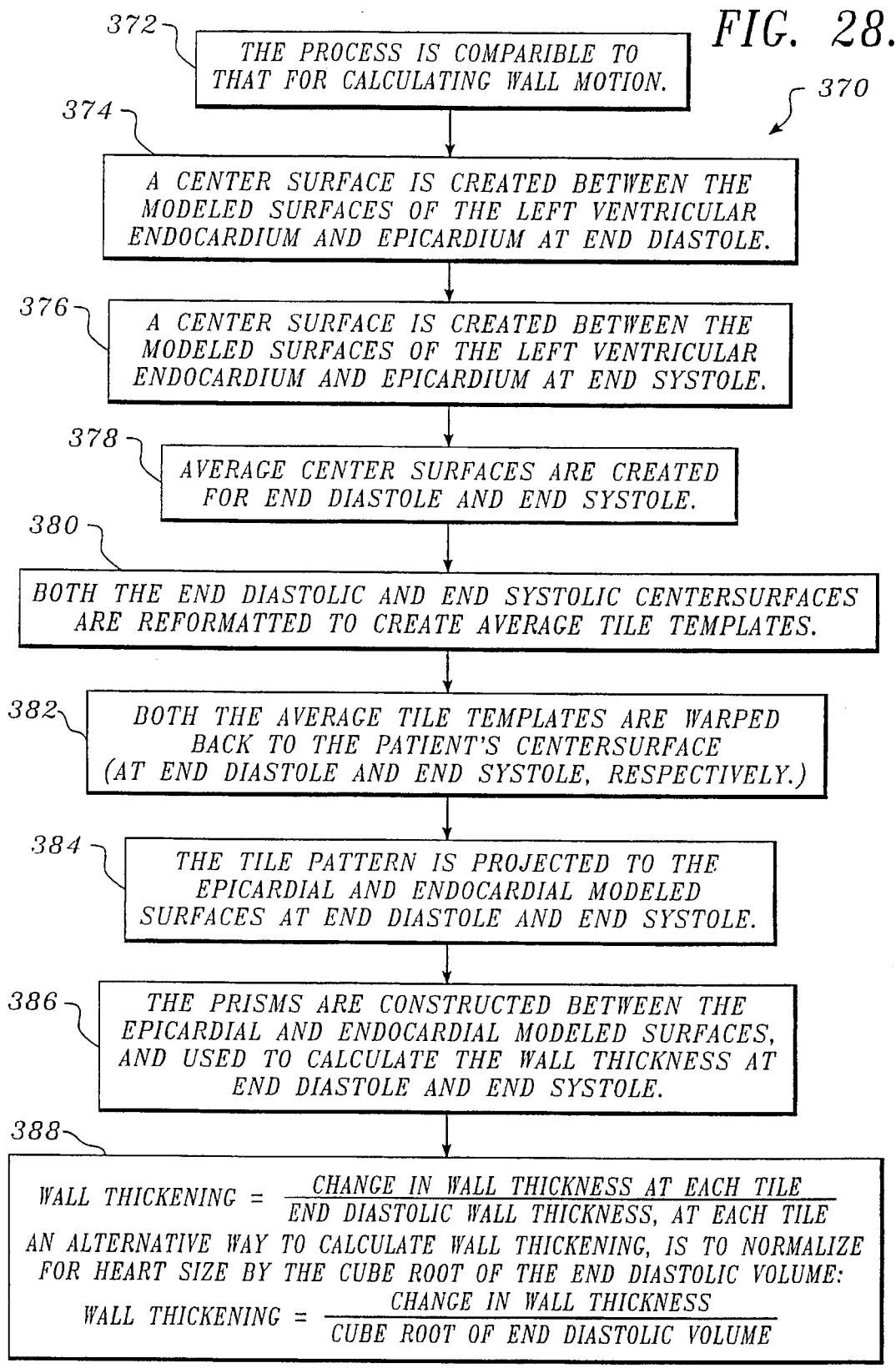
FIG. 28 is a flow chart of the steps used to determine regional wall thickening.

As noted in a block 372, a similar process is used to determine regional wall thickening, in accordance with a flow chart 370 in FIG. 28. A block 374 provides that the center surface is created between the modeled left ventricular endocardium and epicardium surfaces at end diastole, using one of the three methods discussed above. In a block 376, a center surface is also created between the modeled left ventricular endocardium and epicardium surfaces at end systole, again following the procedures already explained above.

A block 378 provides for averaging center surfaces that are created for end diastole and end systole. In a block 380, both the end diastolic and end systolic center surfaces are reformatted to create tiled templates so that in a block 382, both of the tiled templates are warped back to the patient's center surface at end diastole and end systole, respectively. It should be noted that the steps in blocks 378 through 382 are not required if the third method is used to define the center surface. Subsequently, in a block 384, the tile pattern created by warping the templates onto the patient's center surface (for a center surface created by the first two methods) or the mesh of triangles representing the center surface (created by the third method) is projected onto the epicardial and endocardial modeled surfaces at end diastole and end systole. Triangular prisms are then constructed between the epicardial and endocardial modeled surfaces, and, in a block 386, are used to determine wall thickening based on the changes in wall thickness between end diastole and end systole.

Specifically, as noted in a block 388, wall thickening is equal to the change in wall thickness at each tiled section divided by the end diastolic wall thickness at that tiled section. Alternatively, wall thickening can be determined by normalizing for a given heart size by the cube root of the end diastolic volume so that wall thickening is equal to the change in wall thickness divided by the cube root of the end diastolic volume.

Figure 29:
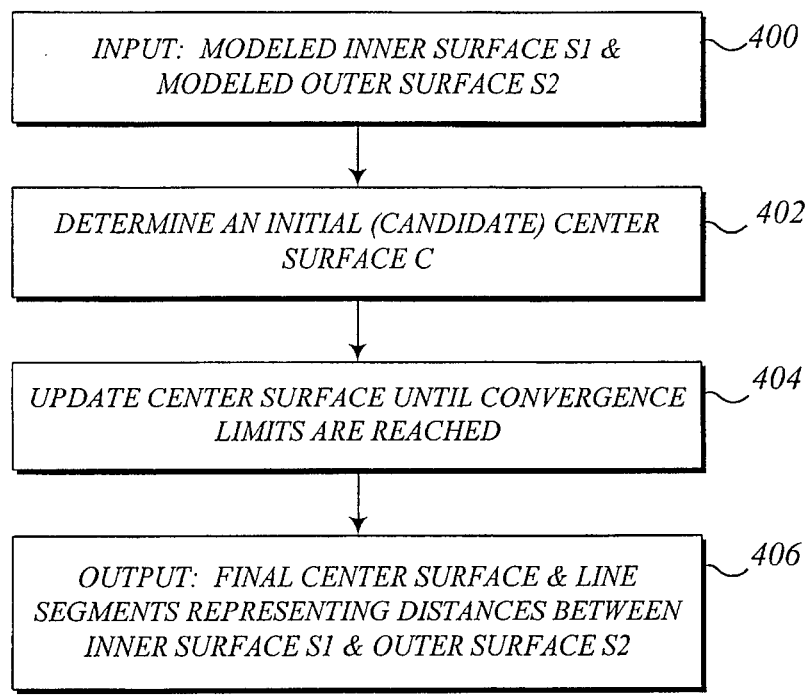
FIG. 29 is an overview flow chart broadly indicating the logic implemented in another method for determining the center surface.
Figure 32:
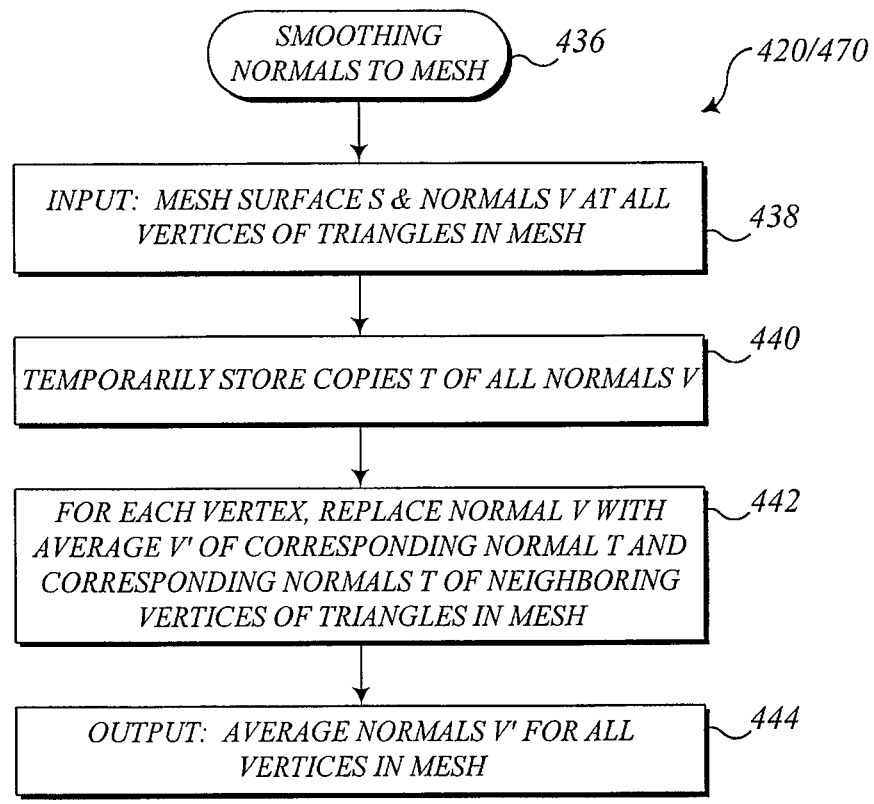
FIG. 32 is a flow chart for a routine used to smooth normals in a mesh.

FIG. 29 broadly discloses the steps that are carried out in the third method to determine a center surface represented by a mesh of connected triangles, which was briefly discussed above. As noted in FIG. 29 in a block 400, the procedure begins with the input of the modeled inner surface, S1, and the modeled outer surface, S2. A block 402 provides for determining the initial (first candidate) center surface, C. The details of the step in block 402 are illustrated in FIGS. 30 through 32 and by reference to a portion of a wall of the heart on which an example of this method is illustrated in FIG. 36.

Figure 30:
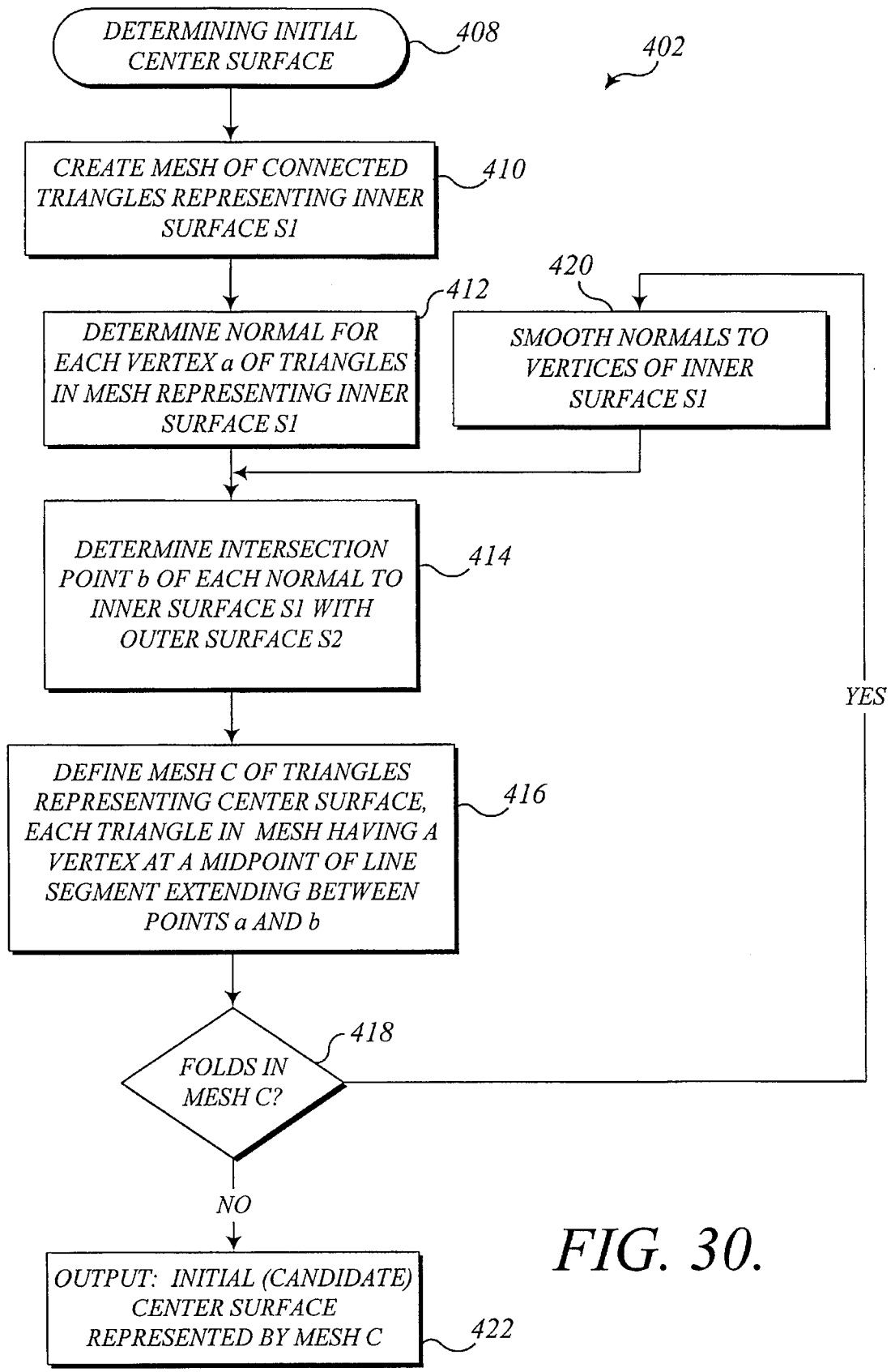
FIG. 30 is a flow chart of the steps for determining an initial or candidate center surface.
Figure 31:
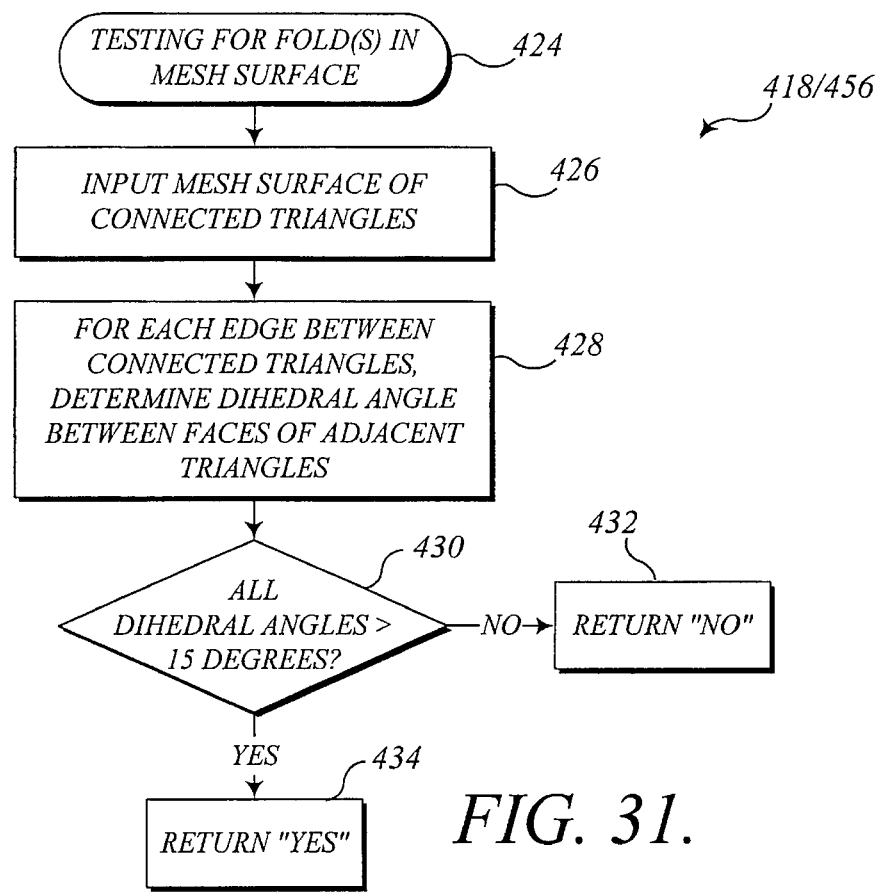
FIG. 31 is a flow chart for a routine that tests for folds in a mesh of triangles defining a surface.

Turning first to FIG. 30, the steps for determining the initial center surface are shown, as indicated by a title block 408. A block 410 provides for creating the mesh of connected triangles 502 representing the inner surface S1, as discussed above in connection with FIG. 35 and as further shown in a mesh 522 representing inner surface S1 in FIG. 36. The normals for each vertex, a, on mesh 522 are determined as noted in a block 412. This step is implemented as discussed above, in regard to determining normals 506 for each vertex 508 in FIG. 35.

A block 414 provides for determining an intersection point, b, on outer surface, S2, by extending each normal as a line segment 510 until it intersects the outer surface. Next, in a block 416, the initial center surface C is defined by creating a mesh 524 of triangles approximately midway between the inner and outer surfaces. Mesh 524 is formed by connecting midpoints, c, of each of line segment 510. Note that in a mathematical sense, points a and b each have three-dimensional coordinates; thus, the midpoint is simply the average of the two sets of coordinates for points a and b for each line segment 510. If the line segment extending along a vertex normal from the inner surface does not intersect the outer surface S2, then any edges or faces of a triangle that would have been formed at the midpoint of the line segment are deleted or not used in defining mesh 524 that represents center surface C.

Figure 37:
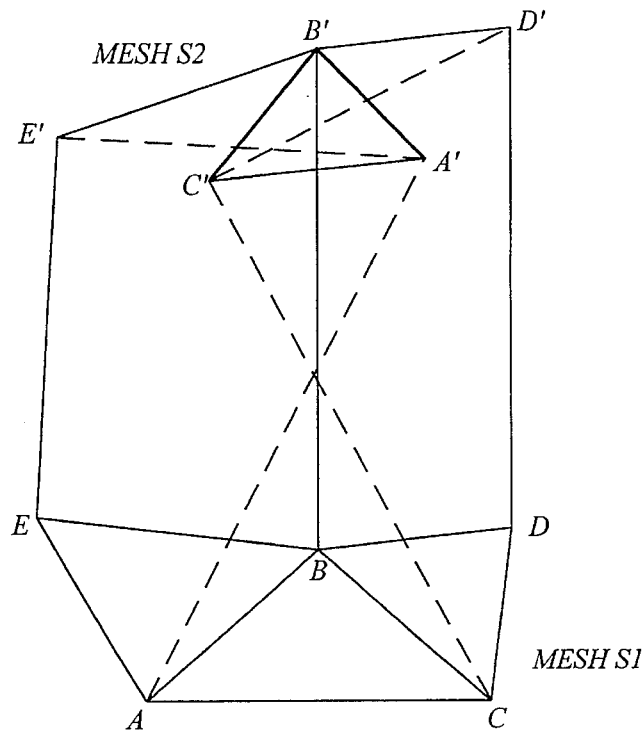
FIG. 37 is a geometric example illustrating how the vertex normals extending from one surface to a second surface can cause a projection of triangles onto the second surface to become reversed so that the triangles on the second surface are folded.

A decision block 418 indicates that a check is next made to determine if any "folds" exist in mesh 524 that defines center surface C. A fold is defined as a dihedral angle between the faces of two adjacent connected triangles that is less than or equal to a predefined limit. In the preferred embodiment, the predefined limit for the dihedral angle is 15 degrees, although further testing may lead to an adjustment of that limit. A check is made for folds on the center surface to ensure that none of the triangles comprising mesh 524 representing the center surface is reversed relative to the orientation of the corresponding triangle on mesh 522, which represents the inner surface. FIG. 37 illustrates how, if the vertex normals AA' and CC' of a mesh S1 twist around each other, as do the normals for vertices A and C, which are represented by the vertical dash lines in the figure, the face of triangle ABC will be reversed or flipped when mapped to a mesh S2. When this happens, then the dihedral angle between the face of triangle A'B'C' and the face of triangle A'B'E' will be very acute (less than 15 degrees), as will the dihedral angle between triangle A'B'C' and B'C'D', forming folds in surface of mesh S2.

The details of a general routine carried out in decision block 418 in FIG. 30, to determine whether a fold exists, are shown in FIG. 31, as noted by a title 424. In a block 426, the mesh of connected triangles (on the center surface C) are input. Next, in a block 428, for each edge between the connected triangles, the dihedral angle is measured between the faces of the adjacent triangles that are joined by the common edge. A decision block 430 determines if all of the dihedral angles are greater than 15 degrees (or other appropriate predefined limit). If the response is no, a block 432 returns a negative response from the routine; otherwise, a block 434 returns a positive response.

Referring back to FIG. 30, if the routine for checking for a fold in center surface C finds that one or more folds exist, the logic proceeds to a block 420. Alternatively, if no fold is found, the logic continues with a block 422 so that the initial (candidate) center surface is provided as an output. Block 420 indicates that normals to inner surface S1 are smoothed. The detailed steps for smoothing normals to a mesh are shown in FIG. 32, as noted by a title block 436.

The input to the routine for smoothing normals include a mesh surface, S, and the normals, V at each of the vertices of triangles comprising the mesh surface, as noted in a block 438. A block 440 indicates that copies T of all normals V in the mesh surface are temporarily stored. In a block 442, for each vertex in the mesh surface, the normal V is replaced with an average V' of the normal T of that vertex and the normals T of all neighboring vertices. A vertex is a "neighboring vertex" if a single edge of a triangle connects it to the vertex in question. Finally, the routine for smoothing concludes with the output of the average normals V' for all vertices in the mesh surface, as provided in a block 444.

Turning back to FIG. 30, once the routine for smoothing normals in block 420 is completed, the output is directed back to block 414 to produce a replacement candidate center surface (hopefully, without folds), following the steps described above, but using the averaged normals on the inner surface to determine the direction of line segments generally corresponding to line segments 510. If folds on the center surface are again detected in decision block 418, the routine to smooth the normals in block 420 may be repeated.

Figure 33:
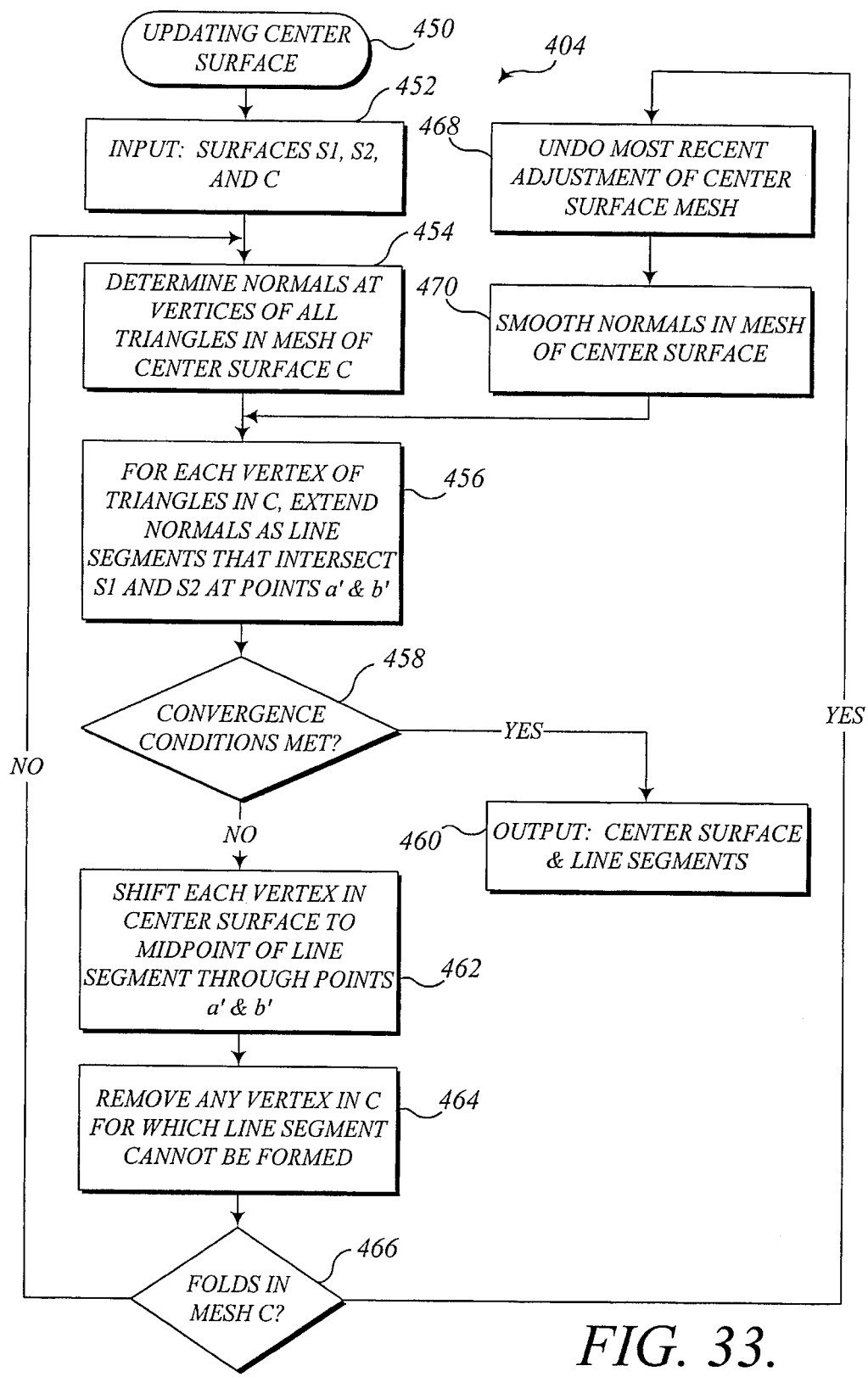
FIG. 33 is a flow chart that illustrates the logic used in updating the center surface.
Figure 34:
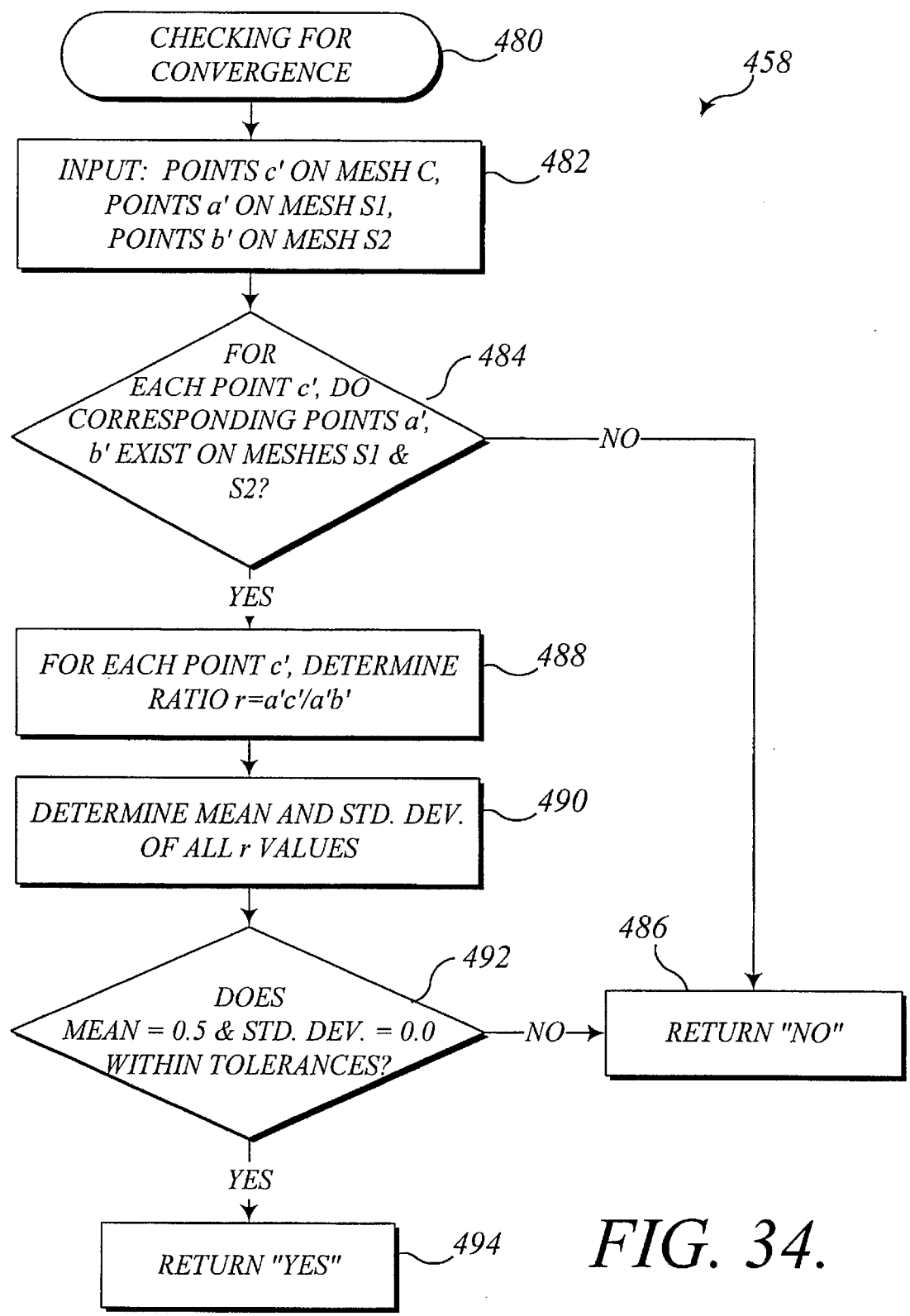
FIG. 34 is a flow chart that illustrates the steps of a routine that determines if the updated center surface is within limits established by predefined criteria.

With reference back to FIG. 29, following the successful output of a candidate center surface from block 402 as described above, a block 404 provides for updating the center surface (repetitively, if necessary) until convergence is achieved within predefined conditions that indicate the accuracy/quality of the center surface. The steps required to implement the updating of the center surface in this manner are shown in FIGS. 33 and 34. In addition, FIG. 36 includes examples illustrating some of the details for adjusting the center surface to achieve convergence within the predefined conditions.

Referring first to FIG. 33, a title block 450 indicates that the following steps are implemented to update (adjust) the center surface. In a block 452, surfaces S1, S2, and C are input. Next, in a block 454, normals at each vertex of the triangles in mesh 524, comprising center surface C are determined. This step is implemented generally following the same steps used to determine the vertex normals for the inner surface, as described above. A block 456 notes that for each vertex of the triangles in the center surface, a line segment 514 is extended along the normal toward the inner and outer surfaces, intersecting them respectively at points a' and b' (as shown in FIG. 36).

A decision block 458 determines if the convergence conditions will be met by the center surface that would be produced by making the current adjustment or update, and if so, a block 460 provides for output of the current center surface. It should be noted that in subsequent loops through this decision block made after an update or adjustment to the center surface, the adjusted center surface C' that meets the convergence conditions would be output in block 460. Details of the steps implemented to determine if the convergence conditions have been met are disclosed in FIG. 34, as indicated by a title 480.

As shown in FIG. 34 at a block 482, the points c' on the mesh representing the center surface, and the points a' and b' at inner and outer surfaces S1 and S2, respectively, are input. A decision block 484 determines for each point c', whether corresponding points a' and b' exist on the inner surface and outer surface meshes, respectively. In other words, does the line segment extending along the vertex normal through each point c' actually intersect corresponding points a' and b' on the inner and outer surfaces. If not, the logic proceeds to a block 486, which returns a negative response (convergence conditions not met) for the check. On the other hand, if the corresponding points exist on the inner and outer surfaces for each of the points on the vertices of the center surface, a block 488 determines for each point c' a ratio r which is equal to a'c'/a'b'. Next, a block 490 provides for determining a mean and a standard deviation for all of the values of r just found in block 488.

A decision block 492 checks the value of the mean and the standard deviation found in block 490 against predefined tolerance limits. Specifically, in the preferred embodiment, the logic determines if the mean is equal to 0.5000 (within four decimal places) and the standard deviation is equal to 0.0000 (within four decimal places). It will be understood that other tolerance limits for the convergence check can alternatively be used. If the convergence does not meet these conditions, block 486 returns a negative response, and conversely, a block 494 returns a positive response if the conditions are met.

Turning again to FIG. 33, a negative response for the check in decision box 458 leads to a block 462, which provides for shifting each vertex of the triangles in the center surface to the midpoint c' of the line segments between points a' and b'. (See FIG. 36.) This adjustment will thus change the mesh representing the center surface. Further, a block 464 removes any vertex in the center surface for which a line segment between the inner surface and the outer surface cannot be formed. Since the outer surface is not closed, it will be apparent that at the mitral valve and other structures in the heart, a line segment through the vertex in the center surface will not always intersect the outer surface.

In such cases, the vertex and adjoined edges are simply eliminated from the center surface mesh in the step of block 464. A decision block 466 indicates that the routine (shown in FIG. 31) is called to check for folds in the center surface mesh. If the routine fails to find a fold, it returns to block 454 to repeat the steps discussed above. However, if a fold is found by the routine, the logic proceeds to a block 468.

In block 468, the most recent adjustment of the center surface mesh is undone, causing the mesh representing the center surface to revert to its previous condition. Then, a block 470 provides for smoothing the normals in the mesh representing the center surface, using the routine shown in FIG. 32, but this time, applying the technique to the vertex normals of the center surface mesh. The logic thereafter returns to block 456 and repeats the steps of adjusting the center surface discussed above. This process repeats reiteratively until the conditions for convergence are met. Once convergence is attained within the predefined tolerance, the logic continues with a block 406, which is shown in FIG. 29. In block 406, the final center surface and the line segments extending between the modeled inner surface S1 and modeled outer surface S2 are output for use in determining cardiac parameters, as described above.

Using eigen shape analyses, the methodology disclosed above can be extended to study shape and shape change in relationship to wall thickening. In addition, an analysis of shape in terms of the cardiac anatomical landmarks can be pursued in terms of geometric components of shape change. These components, called "principal warps" and "relative warps" provide an appropriate generalization to landmark data of principal components and traditional multivariate analysis. The combination of landmark analysis and eigen shape analysis will thus characterize shape and shape change in terms of multiple factors (warps for the landmark data, eigen shapes for the surface analysis).

While the preferred embodiment of the invention has been illustrated and described in connection with preferred embodiments of the invention, it will be appreciated that various changes can be made therein without departing from the spirit and scope of the invention. Accordingly, the scope of the invention should be determined entirely by reference to the claims that follow and should not be limited to the above description.

The embodiments of the invention in which an exclusive property or privilege is claimed are defined as follows:

1. A method for analyzing characteristic cardiac parameters of a patient's heart, comprising the steps of:
    (a) imaging a heart to produce imaging data;
    (b) modeling the heart using the imaging data, producing modeling data corresponding to an inner surface and an outer surface of the heart, at a plurality of times during a cardiac cycle, including at an end systole and at an end diastole of the cardiac cycle;
    (c) using the inner surface of the heart produced with the modeling data, creating a mesh of connected polygons that represent the inner surface of the heart, said polygons including a plurality of connected edges that meet at vertices of the polygons;
    (d) determining a normal for a face of each of the polygons;
    (e) determining a vertex normal for each of the vertices by averaging the normals for the faces of the polygons meeting at the vertices;
    (f) extending the vertex normals as a plurality of line segments that intersect the outer surface at a plurality of points, said line segments extending between the vertices of the polygons on the inner surface and the points on the outer surface;
    (g) connecting midpoints of the line segments to form a mesh having a plurality of connected polygons with vertices disposed at the midpoints of the line segments, said mesh representing the center surface; and
    (h) using the center surface represented by the mesh formed by connecting the midpoints of the line segments, determining characteristic cardiac parameters for the heart.

2. The method of claim 1, further comprising the step of reiteratively adjusting the center surface before it is used in step (h) so that the center surface meets predefined criteria, said predefined criteria indicating that the center surface is substantially centered between the inner and the outer surfaces.

3. The method of claim 2, wherein the step of reiteratively adjusting comprises the steps of:
    (a) for each vertex of the connected polygons comprising the mesh representing the center surface:
        (i) determining an average normal by averaging normals to the polygons surrounding the vertex with a vertex normal for the vertex, said average normal being then extended as a test line segment that intersects the inner surface and the outer surface;
        (ii) comparing a first distance measured between the center surface and one of the inner surface and the outer surface with a sum of the first distance and a second distance, said second distance being measured between the center surface and the outer surface, where both the first distance and the second distance are measured along the test line segment; and
        (iii) moving the vertex of the center surface to a midpoint of the test line segment; and
    (b) accepting the center surface as thus adjusted, for use in step (h) if a last adjustment of the center surface made has enabled the center surface to meet the predefined criteria, and if not, then repeating steps (a)(i) through (a)(iii).

4. The method of claim 3, wherein the predefined criteria are met if:
    (a) the last adjustment of the center surface has not resulted in a connectivity change of the connected polygons extending over the center surface; and
    (b) a mean of a ratio of the first distance to the sum of the first distance and the second distance for all of the vertices on the center surface as last adjusted is substantially equal to 0.5.

5. The method of claim 1, wherein the characteristic cardiac parameters for the heart include at least one of:
    (a) a range of motion for a wall of the heart; and
    (b) a thickness of the wall of the heart.

6. The method of claim 1, wherein the step of imaging the heart includes the steps of:
    (a) digitizing an analog output signal of an imaging device to produce a digital signal;
    (b) graphically displaying images of the inner and the outer surfaces of the heart, produced using the digital signal; and
    (c) tracing borders of the inner and the outer surfaces of the heart on the graphically displayed images to define the imaging data at an end systole and at an end diastole of the cardiac cycle, said center surface being determined using the modeled data for both the end systole and the end diastole.

7. The method of claim 1, wherein the connected polygons comprising both the mesh representing the inner surface and the mesh representing the center surface comprise triangles.

8. The method of claim 1, further comprising the step of determining if a fold exists on the center surface.

9. The method of claim 8, wherein the step of determining if a fold exists comprises the step of determining if a dihedral angle between adjacent polygons on the center surface that are joined along a common edge is less than a predefined value.

10. The method of claim 8, wherein if a fold is found to exist, said method further comprises the steps of:
 (a) for each vertex of the polygons comprising the mesh representing the inner surface:
  (i) determine a smoothing normal by averaging the vertex normal of said vertex with the vertex normals of surrounding vertices; and
  (ii) replacing the vertex normal of said vertex with the smoothing normal; and
 (b) using said smoothing normals as the vertex normals for the mesh representing the inner surface in steps (f) through (h).

11. The method of claim 2, further comprising the step of determining if a fold exists in the center surface after the center surface is reiteratively adjusted.

12. The method of claim 11, wherein the step of determining if a fold exists comprises the step of determining if a dihedral angle between adjacent polygons on the center surface that are joined along a common edge is less than a predefined value.

13. The method of claim 11, wherein if a fold is found to exist in the center surface, said method further comprises the steps of:
 (a) undoing a last adjustment to the center surface;
 (b) for each vertex of the polygons comprising the mesh representing the center surface:
  (i) determining a smoothing normal by averaging the vertex normal of the vertex with the vertex normals of adjacent vertices; and
  (ii) replacing the vertex normal of the vertex with the smoothing normal; and
 (c) using said smoothing normals as the vertex normals for the mesh representing the center surface in determining a subsequent adjustment to the center surface.

14. The method of claim 1, wherein the step of using the center surface to determine characteristic cardiac parameters for the heart comprises the steps of:
 (a) for each vertex on the center surface:
  (i) determining a normal to each connected polygon surrounding said vertex;
  (ii) determining an average vertex normal for said vertex by averaging the normals for the polygons surrounding said vertex;
  (iii) extending the average vertex normals to intersect the inner surface and the outer surface at a plurality of points;
  (iv) connecting the plurality of points on the inner surface to form a plurality of tiled sections on the inner surface; and
  (v) connecting the plurality of points on the outer surface to form a plurality of tiled sections on the outer surface, said tiled sections on the inner surface forming first ends of volumetric elements that extend through the center surface, between the inner surface and the outer surface, and said tiled sections on the outer surface forming second ends of said volumetric elements;
 (b) determining a mean area for the first and the second ends of each of the volumetric elements;
 (c) determining a volume for each of the volumetric elements; and
 (d) as a function of the mean area of the first and second ends and the volume of said volumetric elements, determining a thickness of the cardiac wall at each of the volumetric elements.

15. The method of claim 14, further comprising the step of determining a thickening of the cardiac wall at a volumetric element by analyzing a difference between the thickness of the cardiac wall at the volumetric element at an end diastole and an end systole of the cardiac cycle, where the center surface at the end systole and at the end diastole is used to determine the volumetric elements at the end systole and at the end diastole.

16. A method for determining a center surface that is centered between a first surface and a second surface represents a cardiac wall of a patient's heart, for use in analyzing characteristic cardiac parameters, said method comprising the steps of:
 (a) defining a first mesh of connected polygons representing the first surface, said connected polygons having vertices and edges along which they are connected;
 (b) for each vertex, determining a vertex normal by averaging normals to all of the connected polygons surrounding the vertex;
 (c) extending the vertex normals as line segments that intercept the second surface at a plurality of points;
 (d) creating a second mesh of connected polygons to represent the center surface, by connecting midpoints of the lines segments, said midpoints comprising vertices of said plurality of connected polygons representing the center surface, and
 (e) using said center surface for analyzing characteristic cardiac parameters.

17. The method of claim 16, further comprising the step of reiteratively adjusting the center surface until criteria that determine a quality of the center surface converge to within predefined limits.

18. The method of claim 17, wherein the step of reiteratively adjusting comprises the steps of:
 (a) for each vertex of the connected polygons comprising the second mesh representing the center surface:
  (i) determining an average normal by averaging normals to faces of the connected polygons surrounding said vertex, said average normal being then extended as a test line segment, to intersect the first surface and the second surface;
  (ii) comparing a first distance between the center surface and the first surface with a second distance between the first surface and the second surface, where both the first distance and the second distance are measured along the test line segment; and
  (iii) moving said vertex of the second mesh to a midpoint of the test line segment; and
 (b) accepting the center surface as thus adjusted for use in analyzing the characteristic cardiac parameters, if a last adjustment of the center surface made has enabled the center surface to meet the criteria, and if not, repeating steps (a)(i) through (a)(iii).

19. The method of claim 18, wherein the criteria for convergence are met if:

(a) the last adjustment of the center surface has not resulted in a connectivity change of the connected polygons comprising the second mesh; and (b) a mean of a ratio of the first distance to the second distance for all of the vertices on the center surface as last adjusted is substantially equal to 0.5.

20. The method of claim 16, wherein the connected polygons on the first surface and on the center surface comprise triangles.

21. The method of claim 16, further comprising the step of determining if a fold exists in the second mesh representing the center surface.

22. The method of claim 21, wherein the step of determining if a fold exists comprises the step of determining if a dihedral angle between faces of adjacent polygons comprising the second mesh that are joined along a common edge is less than a predefined value.

23. The method of claim 22, wherein if a fold is found to exist, said method further comprises the steps of:

(a) for each vertex of the polygons comprising the first mesh representing the first surface:

(i) determine a smoothing normal by averaging the vertex normals of said vertex with the vertex normal of surrounding vertices; and (ii) replacing the vertex normal of said vertex with the smoothing normal; and (b) using said smoothing normals as the vertex normals for the first mesh representing the first surface in steps (c) through (d).

24. The method of claim 17, further comprising the step of determining if a fold exists in the center surface after a last adjustment to the center surface was made.

25. The method of claim 24, wherein the step of determining if a fold exists comprises the step of determining if a dihedral angle between faces of adjacent polygons on the center surface that are joined along a common edge is less than a predefined value.

26. The method of claim 24, wherein if a fold exists in the center surface, said method further comprises the steps of:

(a) undoing a last adjustment to the center surface;

(b) for each vertex of the polygons comprising the second mesh representing the center surface:

(i) determining a smoothing normal by averaging the vertex normal of said vertex with the vertex normals of surrounding vertices; and (ii) replacing the vertex normal of said vertex with the smoothing normal; and (c) using said smoothing normals as the vertex normals for the second mesh that represents the center surface in a subsequent adjustment of the center surface.

* * * * *